(12) United States Patent
Strongin et al.

(10) Patent No.: US 9,266,828 B2
(45) Date of Patent: Feb. 23, 2016

(54) INHIBITORS OF FURIN AND OTHER PRO-PROTEIN CONVERTASES

(71) Applicant: Sanford-Burnham Medical Research Institute, La Jolla, CA (US)

(72) Inventors: Alex Strongin, La Jolla, CA (US); Maurizio Pellecchia, La Jolla, CA (US); Elisa Barile, La Jolla, CA (US)

(73) Assignee: SANFORD-BURNHAM MEDICAL RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 14/385,714

(22) PCT Filed: Mar. 14, 2013

(86) PCT No.: PCT/US2013/031733
§ 371 (c)(1),
(2) Date: Sep. 16, 2014

(87) PCT Pub. No.: WO2013/138665
PCT Pub. Date: Sep. 19, 2013

(65) Prior Publication Data
US 2015/0073054 A1 Mar. 12, 2015

Related U.S. Application Data

(60) Provisional application No. 61/611,967, filed on Mar. 16, 2012.

(51) Int. Cl.
| | |
|---|---|
| C07C 279/04 | (2006.01) |
| A61K 31/155 | (2006.01) |
| A61P 35/00 | (2006.01) |
| C07C 317/50 | (2006.01) |
| A61K 38/00 | (2006.01) |
| C07K 5/09 | (2006.01) |
| C07K 5/062 | (2006.01) |

(52) U.S. Cl.
CPC .............. *C07C 317/50* (2013.01); *A61K 38/00* (2013.01); *C07K 5/06034* (2013.01); *C07K 5/0817* (2013.01)

(58) Field of Classification Search
None
See application file for complete search history.

(56) References Cited

FOREIGN PATENT DOCUMENTS
| | | |
|---|---|---|
| WO | WO2013/138665 | 9/2013 |
| WO | WO2013/138666 | 9/2013 |

OTHER PUBLICATIONS

Becker et al., "Potent Inhibitors of Furin and Furin-like Proprotein Convertases Containing Decarboxylated P1 Arginine Mimetics," J. Med. Chem. 53: 1067-1075 (2009).*
Merck Manual Colorectal Cancer accessed Aug. 21, 2014 at URL merckmanuals.com/home/digestive_disorders/tumors_of_the_digestive_system/colorectal_cancer.html).*
Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh.*
Merck Manual Breast Cancer accessed Aug. 21, 2014 at URL: merckmanuals.com/home/womens_health_issues/breast_disorders/breast_cancer.html).*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html.*
National Institute of Cancer—understanding and related topics, accessed Aug. 21, 2014 at URL: cancer.gov/cancertopics/understandingcancer.*
(Merck Manuals Brain Tumors accessed Aug. 21, 2014 at URL merckmanuals.com/home/brain_spinal_cord_and_nerve_disorders/tumors_of_the_nervous_system/brain_tumors.html).*
Merck Manual Skin Cancer accessed Jun. 9, 2015 at URL: merckmanuals.com/professionial/dermatologic-disorders/cancers-of-the-skin/overview-of-skin-cancer.*
Merck Manual Skin Cancer accessed Jun. 9, 2015 at URL: merckmanuals.com/professionial/dermatologic-disorders/cancers-of-the-skin/squamous-cell-carcinoma.*
Merck Manual Lung Cancer accessed Jun. 9, 2015 at URL: merckmanuals.com/home/ pulmonary-disorders/tumors-of-the-lungs/lung-carcinoma.html.*
Medline Plus—Autoimmune disorders—accessed Jun. 22, 2015 at URL: nlm.nih.gov/medlineplus/ency/article/000816.htm.*
Medzhitov, "Origin and physiological roles of inflammation," Nature 454:428-435 (2008).*
Bennett et al., "A Furin-like Convertase Mediates Propeptide Cleavage of BACE, the Alzheimer's b-Secretase," J. Biol. Chem. 275:37712-37717 (2000).*
Stawowy et al., "Proprotein convertases furin and PC5: targeting atherosclerosis and restenosis at multiple levels," J. Mol. Med. 83:865-875 (2005).*
Ma et al., "Effect of Furin inhibitor on lung adenocarcinoma cell growth and metastasis," Canc. Cell Intl 14(43):1-6 (2014).*
Remacle et al., "Selective and potent furin inhibitors protect cells from anthrax without significant toxicity," Int J Biochem Cell Biol. 42(6):987-995 (2010).*
Becker et al., "Highly Potent Inhibitors of Proprotein Convertase Furin as Potential Drugs for Treatment of Infectious Diseases," J. Biol. Chem. 287:21992-22003 (2012).*
Mercapide et al., "Inhibition of Furin-mediated Processing Results in Suppression of Astrocytoma Cell Growth and Invasiveness," Clin. Canc. Res. 8:1740-1746 (2002).*

(Continued)

*Primary Examiner* — Julie Ha
*Assistant Examiner* — Kristina M Hellman
(74) *Attorney, Agent, or Firm* — Wilson Sonsini Goodrich & Rosati

(57) ABSTRACT

Disclosed herein are Furin/PC inhibitors for inhibiting Furin and other Propprotein Convertases. Method of making the Furin/PC inhibitors, chemical and biological characterization of the Furin/PC inhibitors, and the use of the Furin/PC inhibitors to treat infectious diseases, cancers, and inflammatory/autoimmune disorders, are also disclosed.

11 Claims, 14 Drawing Sheets

(56) References Cited

OTHER PUBLICATIONS

Khatib et al., "Inhibition of Proprotein Convertases is Associated with Loss of Growth and Tumorigenicity of HT-29 Human Colon Carcinoma Cells: Importance of Insulin-Like Growth Factor-1 (IGF-1) Receptor Processing in IGF-1-Mediated Functions," J. Biol. Chem. 276(33):30686-30693 (2001).*

Bassi et al., "Furin inhibition results in absent or decreased invasiveness and tumorigenicity of human cancer cells," PNAS 98(18):10326-10331 (2001).*

PCT/US2013/031733 International Preliminary Report on Patentability dated Sep. 14, 2014.

PCT/US2013/031733 International Search Report and Written Opinion dated Mar. 14, 2013.

PCT/US2013/031737 International Search Report and Written Opinion dated Mar. 14, 2013.

PCT/US2013/031737 International Preliminary Report on Patentability dated Sep. 16, 2014.

* cited by examiner

INHIBITORS OF FURIN AND OTHER PRO-PROTEIN CONVERTASES

CROSS-REFERENCE

The present application is the National Phase entry of International Application No. PCT/US 2013/031733, filed Mar. 14, 2013, which claims the benefit of U.S. Provisional Application No. 61/611,967, filed on Mar. 16, 2012, both of which are incorporated herein by reference in their entireties.

BACKGROUND

Furin belongs to the subtilisin-like proprotein convertase family. Furin is a proprotein convertase that processes latent precursor proteins into their biologically active products. It is a calcium-dependent serine endoprotease that cleaves precursor proteins at their paired basic amino acid processing sites. Some of the Furin substrates are: proparathyroid hormone, transforming growth factor beta 1 precursor, proalbumin, pro-beta-secretase, membrane type-1 matrix metalloproteinase, beta subunit of pro-nerve growth factor and von Willebrand factor.

SUMMARY OF THE DISCLOSURE

Disclosed herein, in certain embodiments, are compounds having the general structure I or pharmaceutically acceptable salts thereof: A compound of Formula I, or a pharmaceutically acceptable salt, stereoisomer, tautomer, or prodrug thereof:

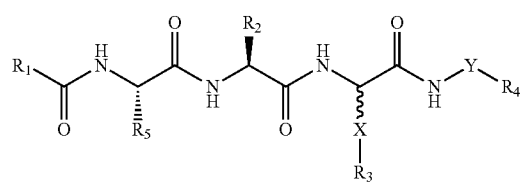

(I)

wherein
  $R_1$ is alkyl, cycloalkyl, heteroalicyclyl, aryl, or heteroaryl;
  $R_2$ is alkyl, cycloalkyl, or heteroalicyclyl;
  $R_3$ is —Z-guanidine or —Z—C(NH$_2$)=NH, wherein Z is aryl or heteroaryl;
  $R_4$ is —W—C(NH$_2$)=NR', wherein W is aryl, thiophenyl, furanyl, oxazolyl, pyrrolyl, or picolinyl; and wherein R' is hydrogen or hydroxyl;
  $R_5$ is —U-guanidine, wherein U is alkyl, cycloalkyl, heteroalicyclyl, aryl, or heteroaryl;
  X=—CH$_2$—, —CH$_2$—CH$_2$—, —CH$_2$NHC(=O)—, —CH$_2$CH$_2$C(=O)NH—, or —CH$_2$C(=O)NH—;
  Y is —CH$_2$—, —S(=O)$_2$—, or —C(=O)—.

In some embodiments of the compound of Formula I, R' is hydrogen. In some embodiments of the compound of Formula I, R' is hydroxyl. In some embodiments of the compound of Formula I, $R_1$ is a $C_1$-$C_6$ alkyl. In some embodiments of the compound of Formula I, $R_1$ is methyl. In some embodiments of the compound of Formula I, $R_2$ is a $C_1$-$C_6$ alkyl. In some embodiments of the compound of Formula I, $R_2$ is isopropyl. In some embodiments of the compound of Formula I, U is $C_1$-$C_6$ alkyl. In some embodiments of the compound of Formula I, U is —(CH$_2$)$_3$—. In some embodiments of the compound of Formula I, X is —CH$_2$—. In some embodiments of the compound of Formula I, $R_3$ is —Z-guanidine. In some embodiments of the compound of Formula I, Z is

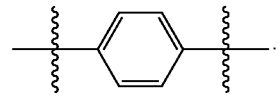

In some embodiments of the compound of Formula I, X is —CH$_2$— and $R_3$ is

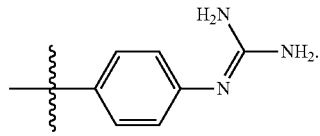

In some embodiments of the compound of Formula I, Y is —CH$_2$—. In some embodiments of the compound of Formula I, W is

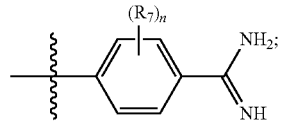

$R_7$ is —F, —CF3, —OCF3, —OCH3, or alkyl; and n is 0, 1, or 2. In a refinement, $R_7$ is —F. In a further refinement, n is 1. In some embodiments, the compound of Formula I is selected from the group consisting of:

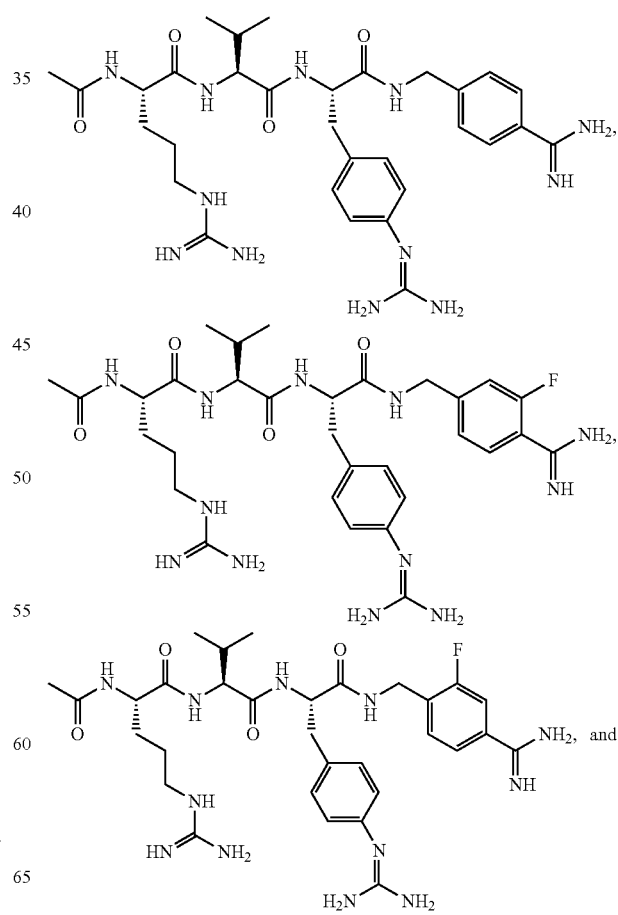

-continued

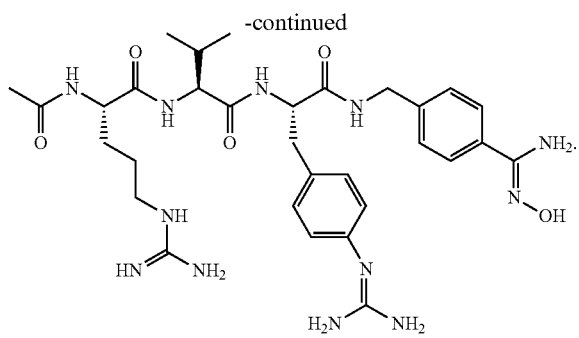

Further disclosed herein, in certain embodiments, are compounds of Formula II, or a pharmaceutically acceptable salt, stereoisomer, tautomer, or prodrug thereof:

(II)

wherein:
$R_1$ is alkyl, cycloalkyl, or heteroalicyclyl;
$R_2$ is —U-guanidine, wherein U is alkyl, cycloalkyl, heteroalicyclyl, aryl, or heteroaryl;
Y is —CONH—, —SO$_2$NH—, —O—, —CH$_2$—, —S—, —SO$_2$—, or —COSO$_2$NH—;
Z is —CONH—, —SO$_2$NH—, —O—, —CH$_2$—, —S—, —SO$_2$—, or —COSO$_2$NH—;
R3 and R4 are each independently —F, —CF$_3$, —OCF$_3$, —OCH$_3$, or alkyl;
a and b are each independently 0, 1, or 2; and
m and n are each independently 0, 1, 2, or 3.

In some embodiments of the compound of Formula II, $R_1$ is $C_1$-$C_6$ alkyl. In some embodiments of the compound of Formula II, $R_1$ is isopropyl. In some embodiments of the compound of Formula II, U is $C_1$-$C_6$ alkyl. In some embodiments of the compound of Formula II, U is —(CH$_2$)$_3$—. In some embodiments of the compound of Formula II, Y is —CONH—. In some embodiments of the compound of Formula II, Z is —SO$_2$NH—. In some embodiments of the compound of Formula II, m is 1 and n is 1. In some embodiments of the compound of Formula II, a and b are 0. In some embodiments, the compound of Formula II is Also disclosed herein, in certain embodiments, are pharmaceutical compositions comprising a Furin/PC inhibitor disclosed herein.

Additionally disclosed herein, in certain embodiments, are methods of treating an infectious disease in a subject in need of such treatment. In some embodiments, the methods comprise administering a therapeutically effective amount of a Furin/PC inhibitor disclosed herein. In some embodiments, the infection disease is associated with influenza virus, human immunodeficiency virus 1, Ebola, measles, cytomegalovirus, and flaviviruses (Dengue, Yellow fever, West Nile, Japanese encephalitis and multiple additional related flaviviruses) and parasitic nematodes. In some embodiments, the Furin/PC inhibitor neutralizes an exotoxin selected from the group consisting of anthrax toxin, pseudomonas exotoxin A, Shiga toxin, diphtheria toxin, tetanus and botulism neurotoxins, and combinations thereof. In some embodiments, the Furin/PC inhibitor neutralizes virulence of bacteria carrying the exotoxin.

Further disclosed herein, in certain embodiments, are methods of treating a cancer in a subject in need thereof. In some embodiments, the methods comprise administering a therapeutically effective amount of a Furin/PC inhibitor disclosed herein. In some embodiments, the cancer is skin tumors, head and neck squamous cell carcinomas, astrocytoma, lung non-small cell carcinoma, or metastasis of colorectal cancer.

Also disclosed herein, in certain embodiments, are methods of treating an autoimmune or inflammatory disease, disorder or condition in a subject in need thereof. In some embodiments, the methods comprise administering a therapeutically effective amount of a Furin/PC inhibitor disclosed herein. In some embodiments, the autoimmune or inflammatory disease is atherosclerosis, arthritis, or Alzheimer's Disease.

BRIEF DESCRIPTION OF THE DRAWINGS

The technical features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

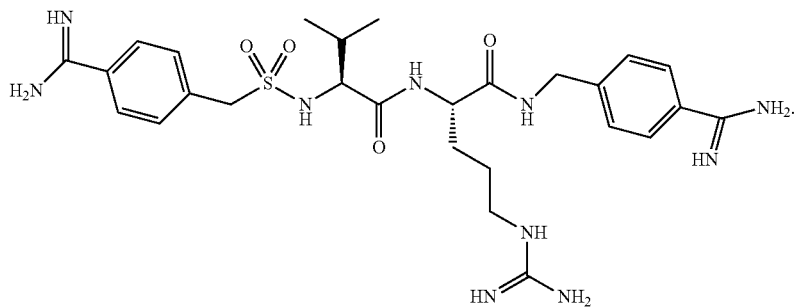 [SMILES: CC(C)[C@H](NS(=O)(=O)Cc1ccc(C(=N)N)cc1)C(=O)N[C@@H](CCCNC(=N)N)C(=O)NCc1ccc(C(=N)N)cc1]

Figure 6:
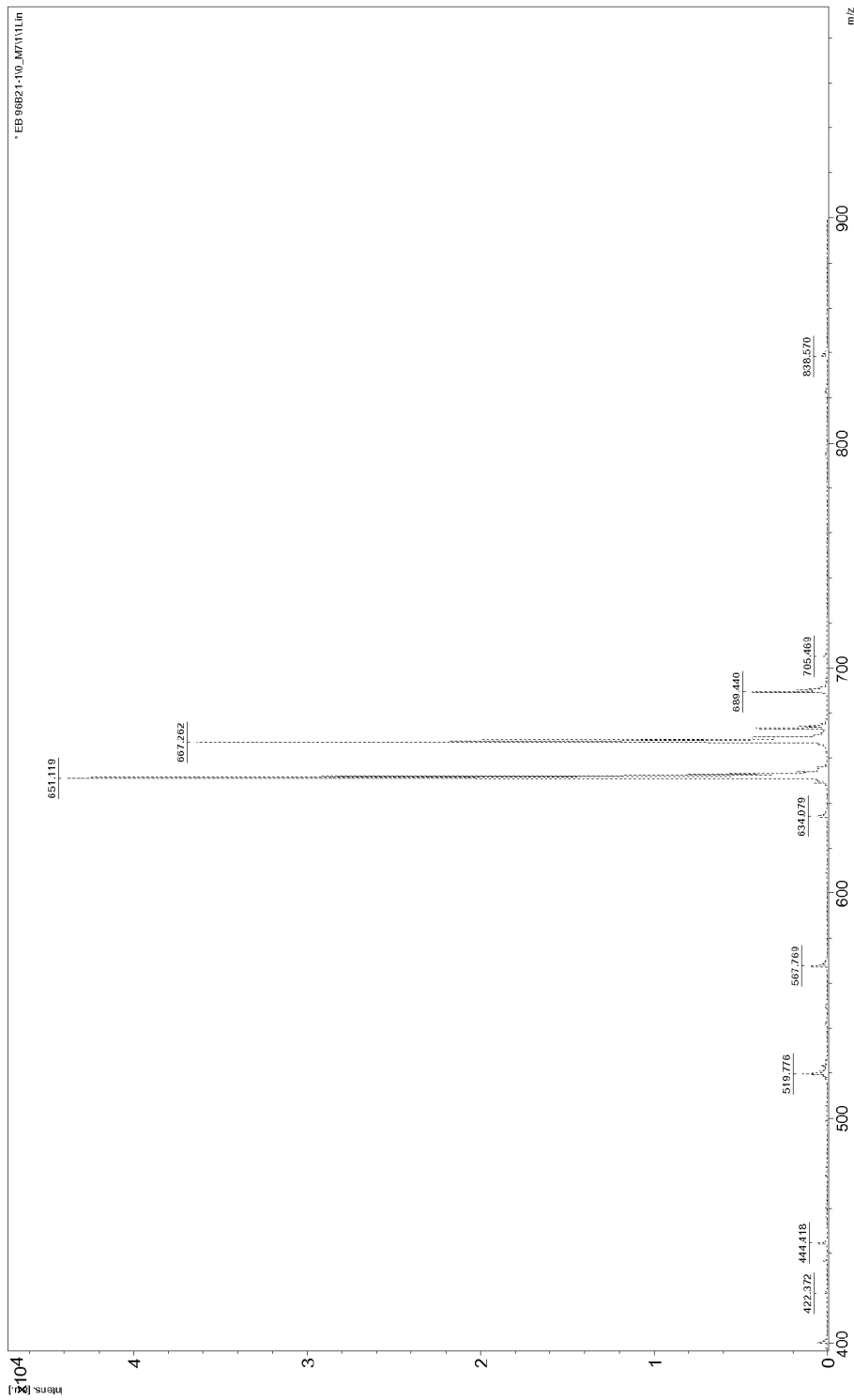
Figure 7:
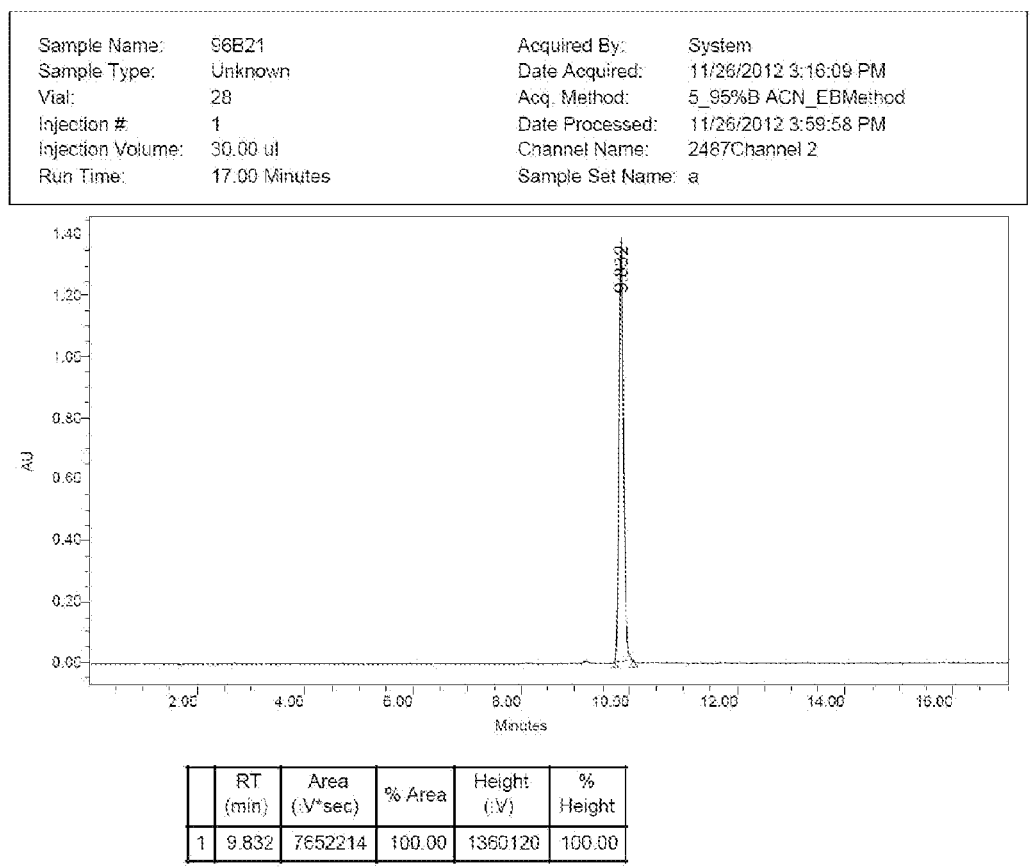
Figure 8:
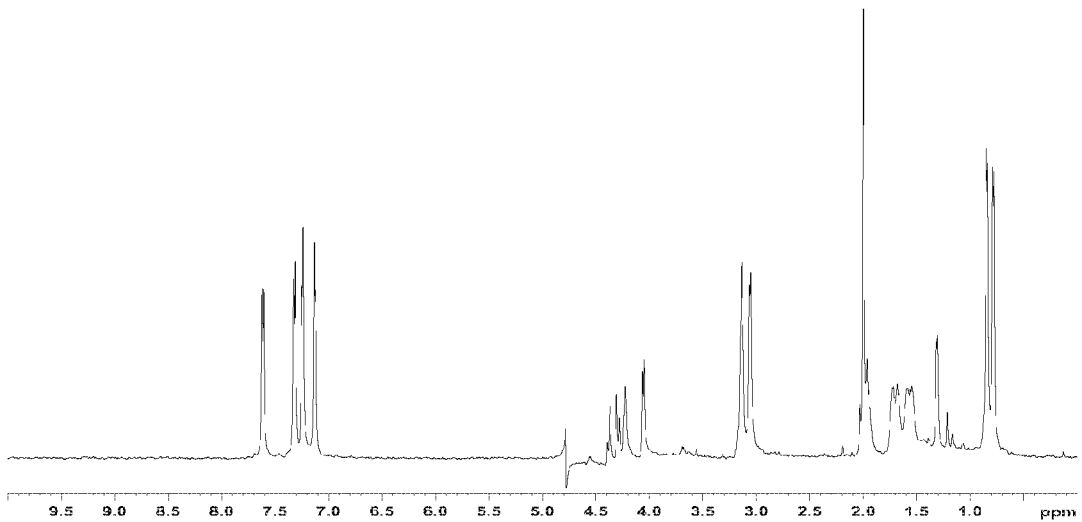
Figure 9:
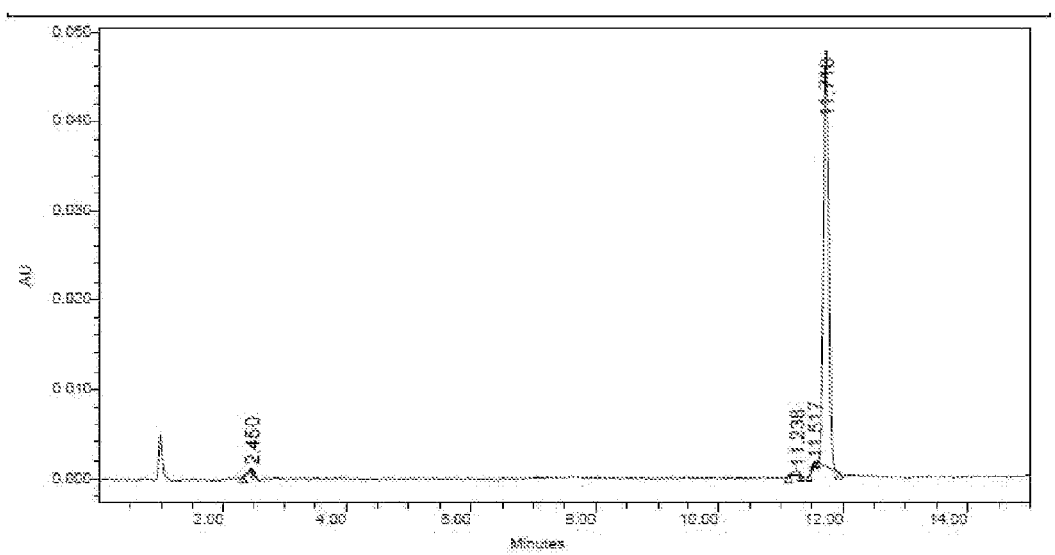

FIG. 6 exemplifies the MS (MALDI) profile of Compound D;

FIG. 7 exemplifies the HPLC profile of Compound D;

FIG. 8 exemplifies the $^1$H NMR spectrum of Compound D in deuterated PBS;

FIG. 9 exemplifies the HPLC profile of Compound E.

Figure 10:
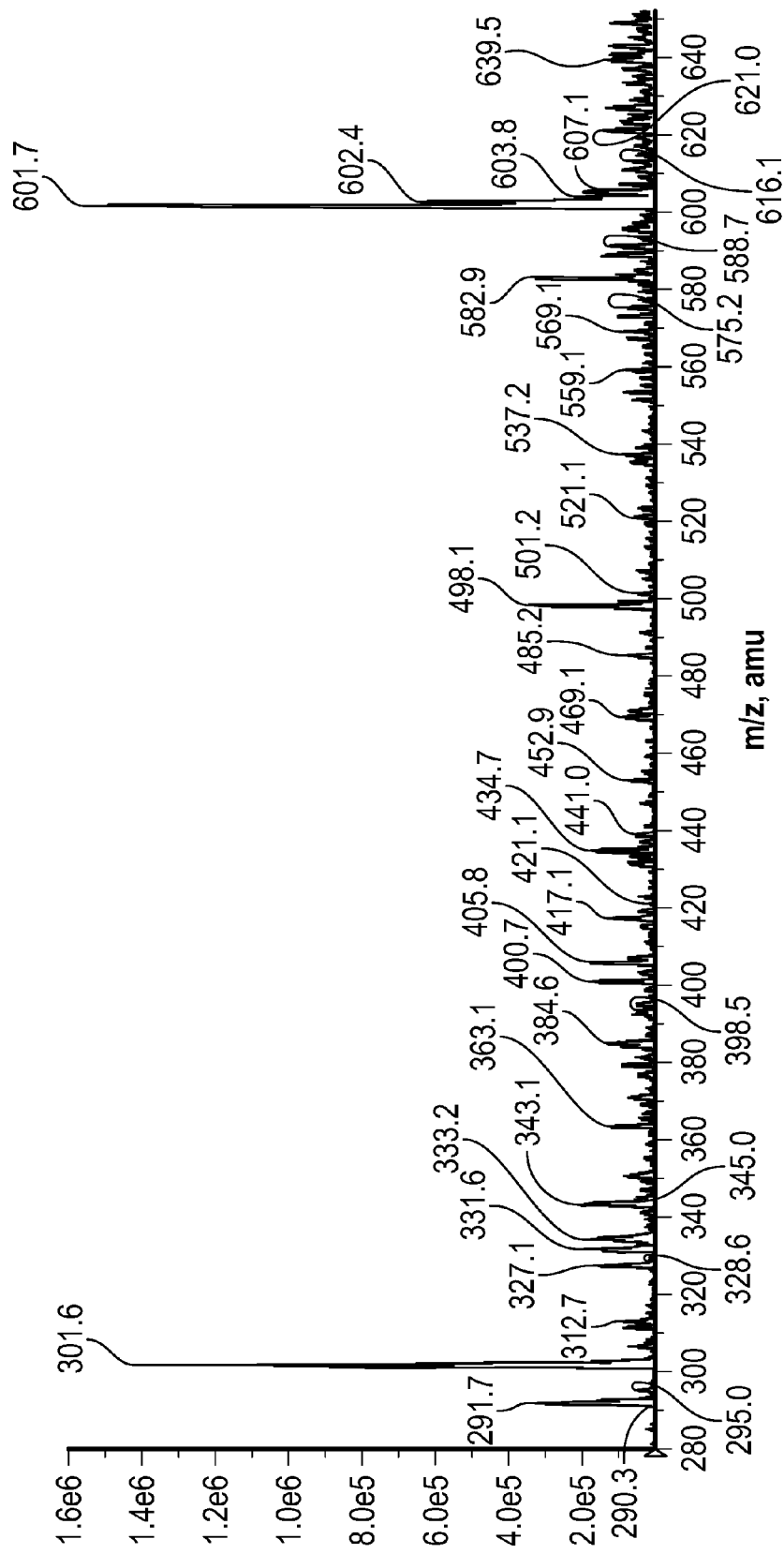

FIG. 10 exemplifies the MS profile of Compound E.

Figure 11:
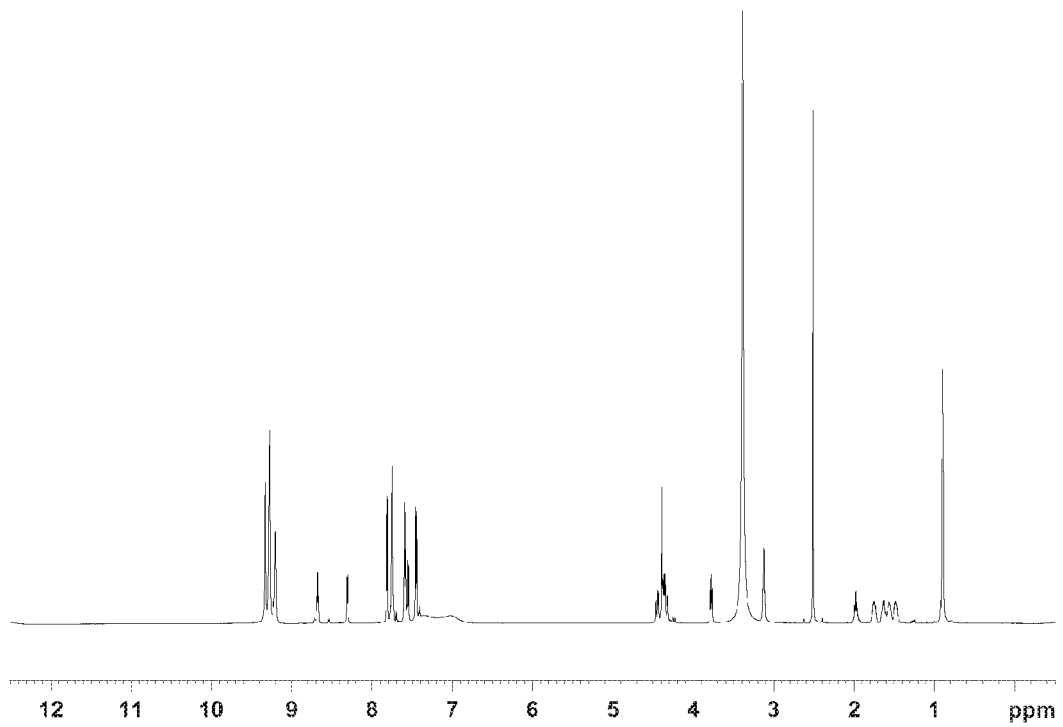
Figure 12:
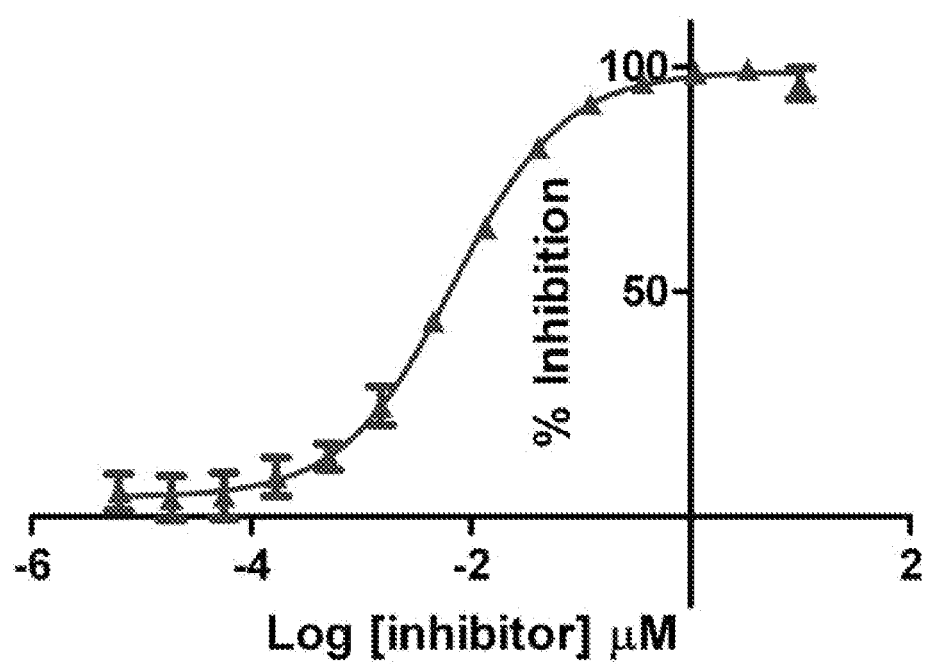
Figure 13:
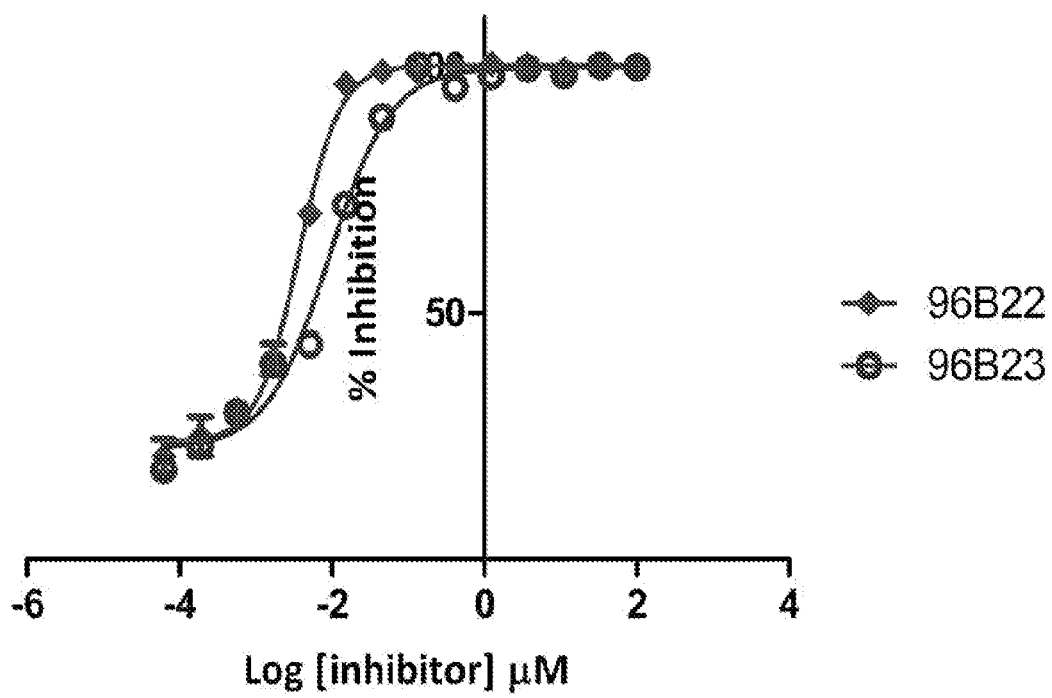
Figure 14:
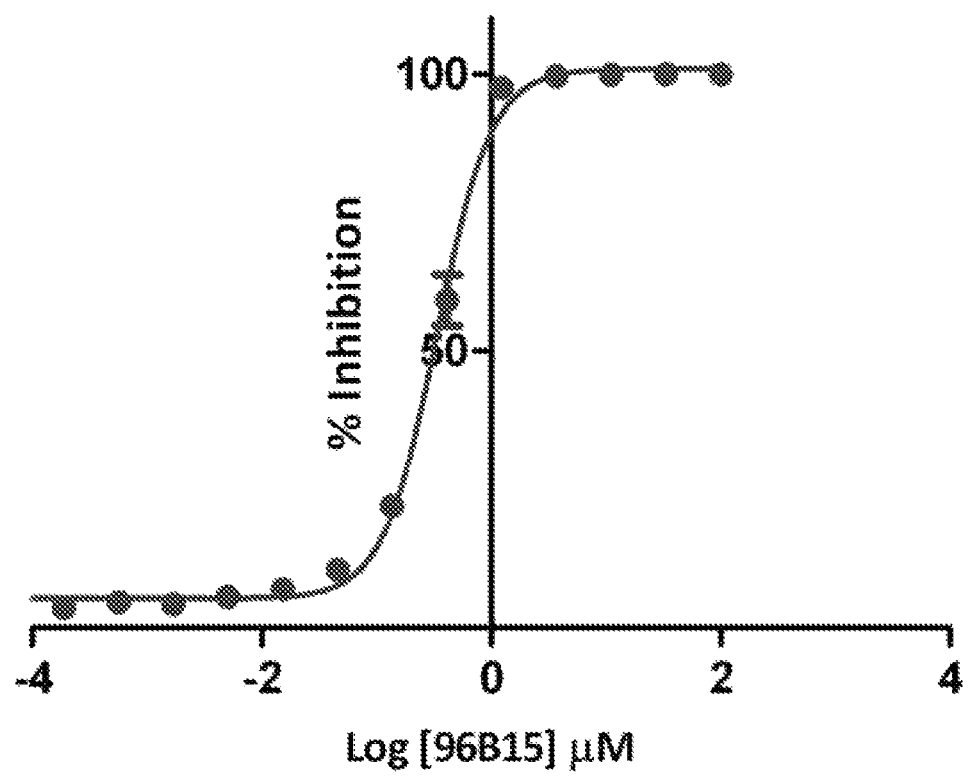

FIG. 11 exemplifies $^1$H NMR spectrum of Compound E in DMSO-d6;

FIG. 12 exemplifies the biochemical assay dose response for Compound A;

FIG. 13 exemplifies the biochemical assay dose response for Compound B and Compound C; and FIG. 14 exemplifies the biochemical assay dose response for Compound E.

DETAILED DESCRIPTION OF THE DISCLOSURE

Proprotein convertases (PCs), such as Furin, plays an important role in diseases such as Alzheimer's disease, cancer, and viral and bacterial infections. Many pathogens depend on the human pro-protein convertase Furin to process their toxins or cell adhesion factors. Accordingly, Furin inhibitors that inactivate these mechanisms in host-pathogen interactions provides an effective route to prevent the initiation or propagation of the infection. Thus, inhibition of furin may provide a feasible and promising approach for therapeutic intervention of furin-mediated disease mechanisms.

There is a need for identifying potent and selective agents for the treatment of various diseases, disorders and pathologies, such as infectious diseases (e.g. influenza and Anthrax), cancers, and neurodegenerative diseases (e.g. Alzheimer).

Proteolysis data have revealed detailed information on Furin and related Furin-like PCs cleavage preferences for their substrates, consisting of multibasic consensus sequences, preferentially located after an arginine residue. Because no small-molecule inhibitors of Furin are currently available, d-Arg-based peptides, α1-antitrypsin Portland, and the synthetic inhibitor decanoyl-Arg-Val-Lys-Arg-chloromethylketone (DEC-RVKR-CMK) have been used to validate the role of Furin in a variety of cellular models.

However, Arg-based peptides such as hexa- and nona-d-Arg have either low or no therapeutic potential because of their intrinsic ability to cross-react with multiple, pathogen and host, proteinase and non-proteinase targets, which are unrelated to Furin.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Ibrutinib, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "subject", "patient" and "individual" are used interchangeably. As used herein, they refer to an animal. By way of example only, a subject may be, but is not limited to, a mammal including, but not limited to, a human. The terms do not require the supervision (whether continuous or intermittent) of a medical professional.

The terms "isolated" and "purified" refer to a material that is substantially or essentially removed from or concentrated in its natural environment. For example, an isolated nucleic acid is one that is separated from the nucleic acids that normally flank it or other nucleic acids or components (proteins, lipids, etc.) in a sample. In another example, a polypeptide is purified if it is substantially removed from or concentrated in its natural environment. Methods for purification and isolation of nucleic acids and proteins are documented methodologies.

The term "optionally substituted" or "substituted" means that the referenced group substituted with one or more additional group(s). In certain embodiments, the one or more additional group(s) are individually and independently selected from amide, ester, alkyl, cycloalkyl, heteroalkyl, aryl, heteroaryl, heteroalicyclic, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, amido.

An "alkyl" group refers to an aliphatic hydrocarbon group. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, iso-propyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. A "lower alkyl" is a $C_1$-$C_6$ alkyl. A "heteroalkyl" group substitutes any one of the carbons of the alkyl group with a heteroatom having the appropriate number of hydrogen atoms attached (e.g., a $CH_2$ group to an NH group or an O group).

An "alkoxy" group refers to a (alkyl)O— group, where alkyl is as defined herein.

The term "alkylamine" refers to the $N(alkyl)_xH_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

An "amide" is a chemical moiety with formula C(O)NHR or NHC(O)R, where R is selected from alkyl, cycloalkyl, aryl, heteroaryl (bonded through a ring carbon) and heteroalicyclic (bonded through a ring carbon).

The term "ester" refers to a chemical moiety with formula —C(=O)OR, where R is selected from the group consisting of alkyl, cycloalkyl, aryl, heteroaryl and heteroalicyclic.

As used herein, the term "aryl" refers to an aromatic ring wherein each of the atoms forming the ring is a carbon atom. Aryl rings described herein include rings having five, six, seven, eight, nine, or more than nine carbon atoms. Aryl groups are optionally substituted. Examples of aryl groups include, but are not limited to phenyl, and naphthalenyl.

The term "cycloalkyl" refers to a monocyclic or polycyclic non-aromatic radical, wherein each of the atoms forming the ring (i.e. skeletal atoms) is a carbon atom. In various embodiments, cycloalkyls are saturated, or partially unsaturated. In some embodiments, cycloalkyls are fused with an aromatic ring. Cycloalkyl groups include groups having from 3 to 10 ring atoms. Illustrative examples of cycloalkyl groups include, but are not limited to, the following moieties:

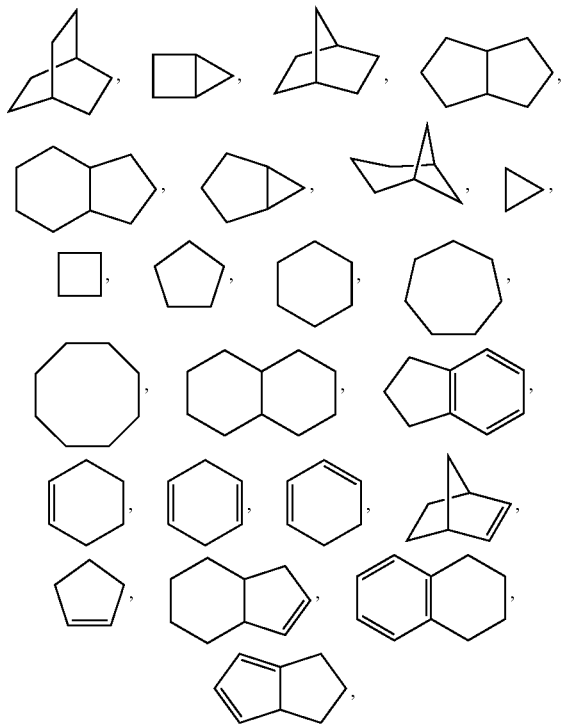

and the like. Monocyclic cycloalkyls include, but are not limited to, cyclopropyl, cyclobutyl, cyclopentyl, cyclohexyl, cycloheptyl, and cyclooctyl. Dicylclic cycloalkyls include, but are not limited to tetrahydronaphthyl, indanyl, tetrahydropentalene or the like. Polycyclic cycloalkyls include adamantane, norbornane or the like. The term cycloalkyl includes "unsaturated nonaromatic carbocyclyl" or "nonaromatic unsaturated carbocyclyl" groups both of which refer to a nonaromatic carbocycle, as defined herein, that contains at least one carbon carbon double bond or one carbon carbon triple bond.

The term "heterocyclic" or "heterocyclyl" refers to heteroaromatic and heteroalicyclic groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In certain embodiments, heteroaryl groups are optionally substituted. In certain embodiments, heteroaryl groups are monocyclic or polycyclic. Examples of monocyclic heteroaryl groups include and are not limited to:

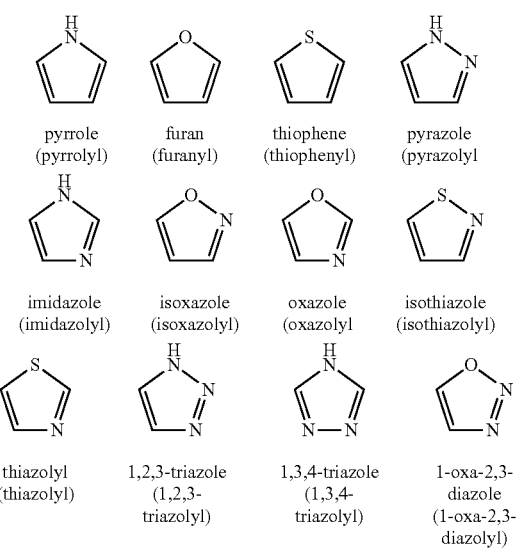

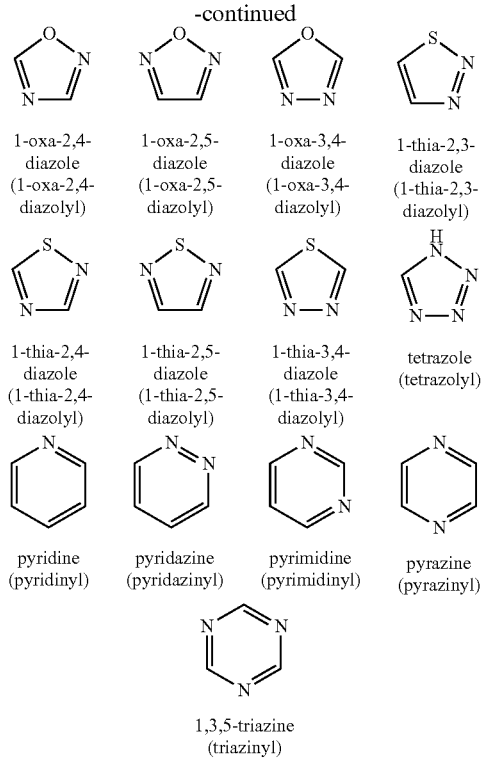
Examples of bicyclic heteroaryl groups include and are not limited to:
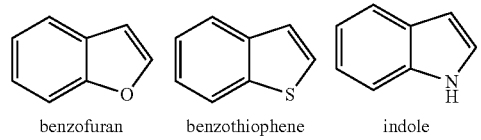
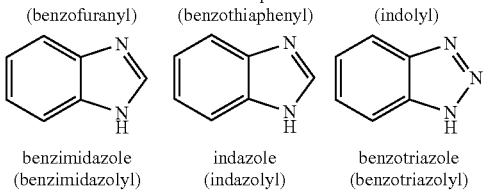
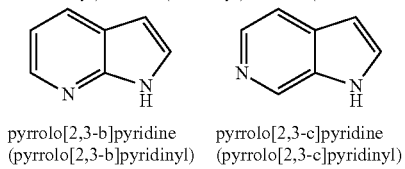
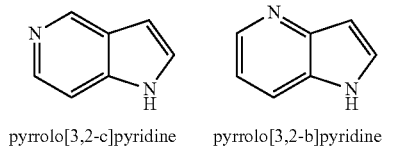
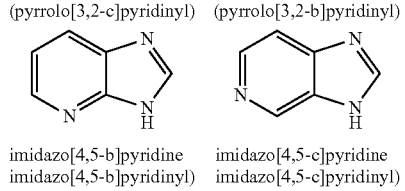
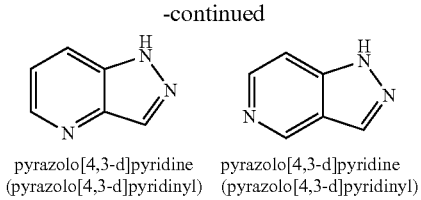
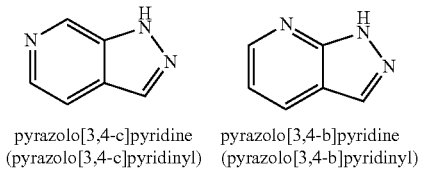
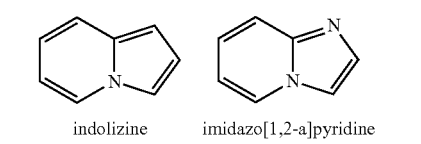
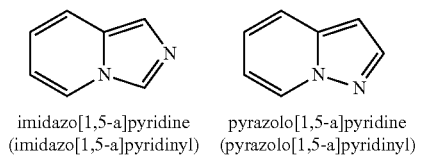
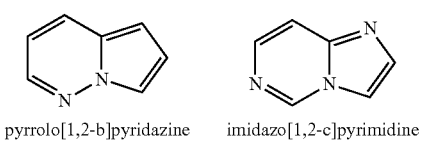
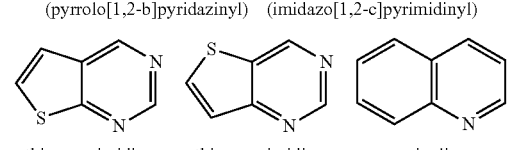
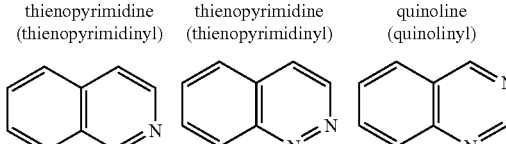
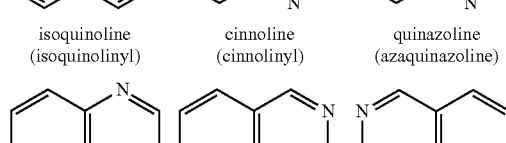
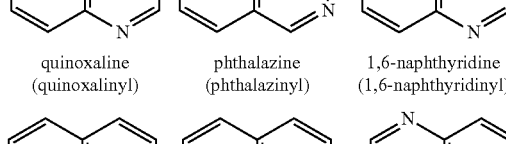

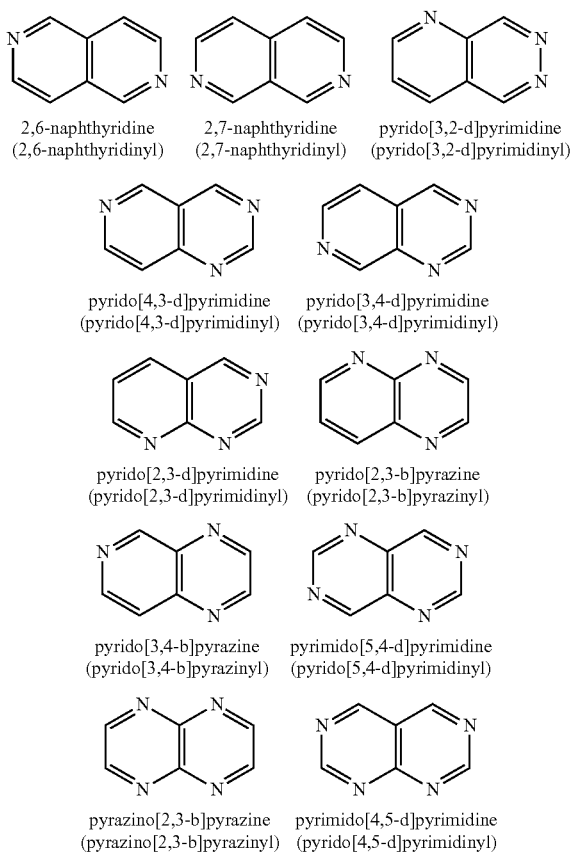

or the like.

A "heteroalicyclic" group or "heterocycloalkyl" group refers to a cycloalkyl group, wherein at least one skeletal ring atom is a heteroatom selected from nitrogen, oxygen and sulfur. In some embodiments, the radicals are fused with an aryl or heteroaryl. Example of saturated heterocyloalkyl groups include

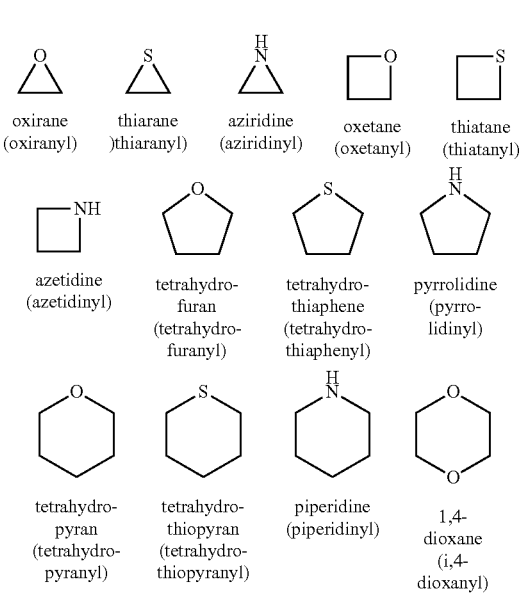

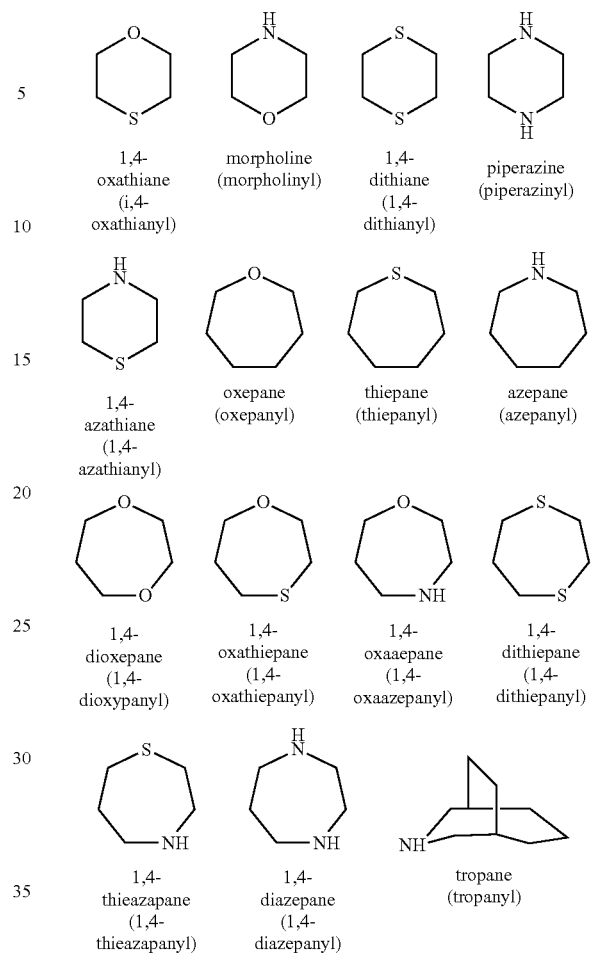

Examples of partially unsaturated heterocycloalkyl groups include

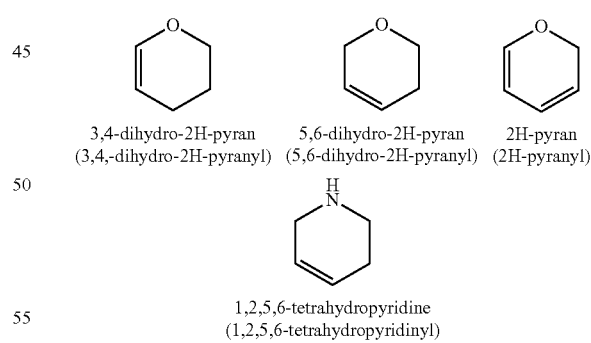

Other illustrative examples of heterocycloalkyl groups, also referred to as non-aromatic heterocycles, include:

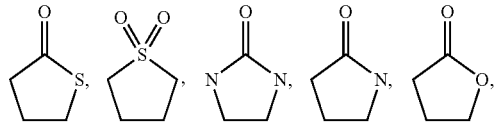

or the like.

The term heteroalicyclic also includes all ring forms of the carbohydrates, including but not limited to the monosaccharides, the disaccharides and the oligosaccharides.

The term "halo" or, alternatively, "halogen" means fluoro, chloro, bromo and iodo.

The terms "haloalkyl," and "haloalkoxy" include alkyl and alkoxy structures that are substituted with one or more halogens. In embodiments, where more than one halogen is included in the group, the halogens are the same or they are different. The terms "fluoroalkyl" and "fluoroalkoxy" include haloalkyl and haloalkoxy groups, respectively, in which the halo is fluorine.

The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH—CH—O—$CH_3$, —Si($CH_3$)$_3$, —$CH_2$—CH—N—$OCH_3$, and —CH=CH—N($CH_3$)—$CH_3$. In some embodiments, up to two heteroatoms are consecutive, such as, by way of example, —$CH_2$—NH—$OCH_3$ and —$CH_2$—O—Si($CH_3$)$_3$.

A "cyano" group refers to a CN group.

An "isocyanato" group refers to a NCO group.

A "thiocyanato" group refers to a CNS group.

An "isothiocyanato" group refers to a NCS group.

"Alkoyloxy" refers to a RC(=O)O— group.

"Alkoyl" refers to a RC(=O)— group.

Compounds

Provided herein are compounds having the general structure I or pharmaceutically acceptable salts stereoisomers, tautomers, or prodrugs thereof:

wherein $R_1$ is alkyl, cycloalkyl, heteroalicyclyl, aryl, or heteroaryl;

$R_2$ is alkyl, cycloalkyl, or heteroalicyclyl;

$R_3$ is —Z-guanidine or —Z—C($NH_2$)=NH, wherein Z is aryl or heteroaryl;

$R_4$ is —W—C($NH_2$)=NR', wherein W is aryl, thiophenyl, furanyl, oxazolyl, pyrrolyl, or picolinyl; and wherein R' is hydrogen or hydroxyl;

$R_5$ is —U-guanidine, wherein U is alkyl, cycloalkyl, heteroalicyclyl, aryl, or heteroaryl;

X=—$CH_2$—, —$CH_2$—$CH_2$—, —$CH_2$NHC(=O)—, —$CH_2CH_2$C(=O)NH—, or —$CH_2$C(=O)NH—;

Y is —$CH_2$—, —S(=O)$_2$—, or —C(=O)—.

In some embodiments of the compound of Formula I, R' is hydrogen. In some embodiments of the compound of Formula I, R' is hydroxyl. Without wishing to be bound by any particular theory, it is contemplated in the present disclosure that replacement of one or more imino hydrogen (such as in the amidine and/or guanidine moiety) with hydroxyl improves bioavailability in some embodiment. For example, replacement of the carboxylmidamide in position R4 with a N'-hydroxyimidamide improves bioavailability in some embodiments.

In some embodiments of the compound of Formula I, $R_1$ is a $C_1$-$C_6$ alkyl. In some embodiments of the compound of Formula I, $R_1$ is methyl. In some embodiments of the compound of Formula I, $R_2$ is a $C_1$-$C_6$ alkyl. In some embodiments of the compound of Formula I, $R_2$ is isopropyl.

In some embodiments of the compound of Formula I, U is $C_1$-$C_6$ alkyl. In some embodiments of the compound of Formula I, U is —($CH_2$)$_3$—.

In some embodiments of the compound of Formula I, X is —$CH_2$—. In some embodiments of the compound of Formula I, $R_3$ is —Z-guanidine. In some embodiments of the compound of Formula I, Z is In some embodiments of the compound of Formula I, X is —CH₂— and R₃ is

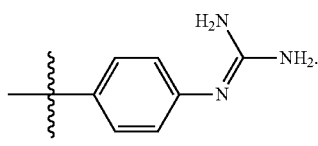 [SMILES: *c1ccc(N=C(N)N)cc1]

In some embodiments of the compound of Formula I, Y is —CH₂—.

In some embodiments of the compound of Formula I, W is

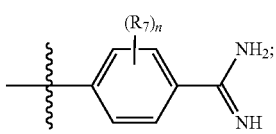

R₇ is —F, —CF₃, —OCF₃, —OCH₃, or alkyl; and n is 0, 1, or 2. In a refinement, R₇ is —F. In a further refinement, n is 1.

In some embodiments, the compound of Formula I is selected from the group consisting of:

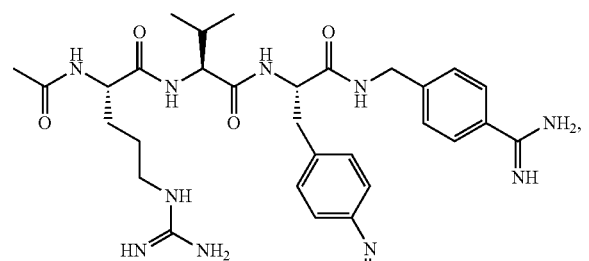

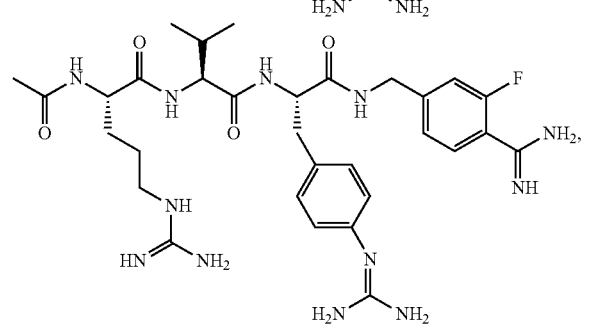

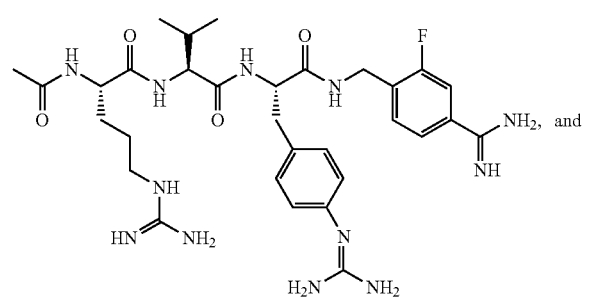

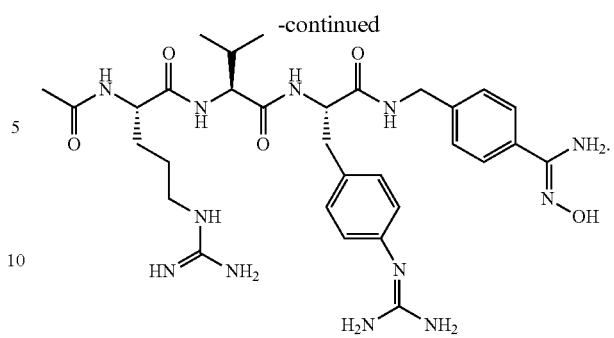

Also disclosed herein, in certain embodiments, are compounds of formula II, or pharmaceutically acceptable salts, stereoisomers, tautomers, or prodrugs thereof:

(II)

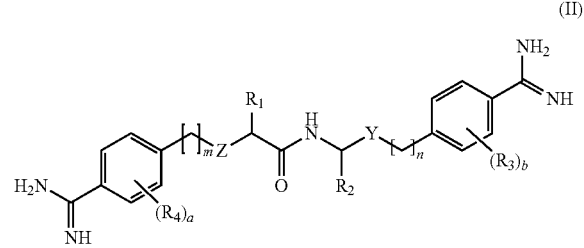

wherein:

R₁ is alkyl, cycloalkyl, or heteroalicyclyl;

R₂ is —U-guanidine, wherein U is alkyl, cycloalkyl, heteroalicyclyl, aryl, or heteroaryl;

Y is —CONH—, —SO2NH—, —O—, —CH2-, —S—, —SO2-, or —COSO2NH—;

Z is —CONH—, —SO₂NH—, —O—, —CH₂—, —S—, —SO₂—, or —COSO₂NH—;

R₃ and R₄ are each independently —F, —CF₃, —OCF₃, —OCH₃, or alkyl;

a and b are each independently 0, 1, or 2; and m and n are each independently 0, 1, 2, or 3.

In some embodiments, the prodrug of the compound in Formula II is formed by replacing one or more imino hydrogen (such as in the amidine and/or guanidine moiety) with hydroxyl. In some embodiments, replacement of one or more imino hydrogen with hydroxyl improves bioavailability. In some embodiments, replacement of the carboxylmidamide in position R₄ with a N'-hydroxyimidamide improves bioavailability.

In some embodiments of the compound of Formula II, R₁ is C₁-C₆ alkyl. In some embodiments of the compound of Formula II, R₁ is isopropyl.

In some embodiments of the compound of Formula II, U is C₁-C₆ alkyl. In some embodiments of the compound of Formula II, U is —(CH₂)₃—.

In some embodiments of the compound of Formula II, Y is —CONH—. In some embodiments of the compound of Formula II, Z is —SO₂NH—. In some embodiments, Y is —CONH— and Z is —SO₂NH—.

In some embodiments of the compound of Formula II, m is 1 and n is 1.

In some embodiments of the compound of Formula II, a is 0 and b is 0.

In some embodiments, the compound of Formula II is
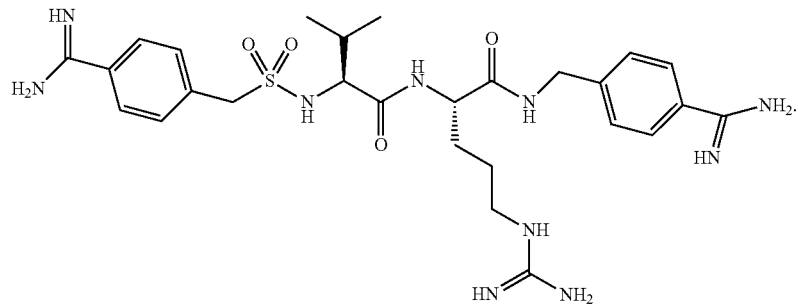 [SMILES: CC(C)[C@H](NS(=O)(=O)Cc1ccc(C(=N)N)cc1)C(=O)N[C@@H](CCCNC(=N)N)C(=O)NCc1ccc(C(=N)N)cc1]
In some embodiments, compounds of Formula I and II are:
| Compound No. | Chemical Structure | IC50 against Furin |
|---|---|---|
| A | 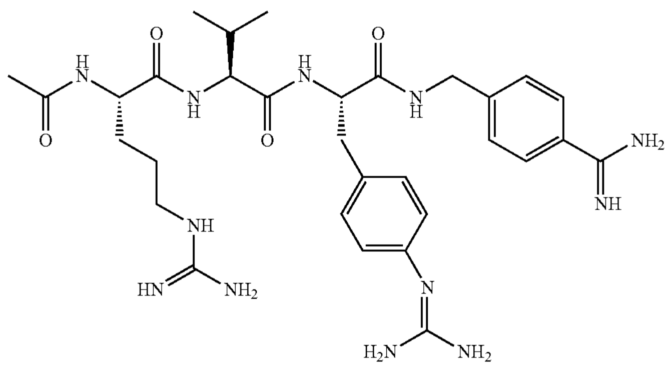 [SMILES: CC(=O)N[C@@H](CCCNC(=N)N)C(=O)N[C@H](C(=O)N[C@@H](Cc1ccc(N=C(N)N)cc1)C(=O)NCc1ccc(C(=N)N)cc1)C(C)C] | 7 nm |
| B | 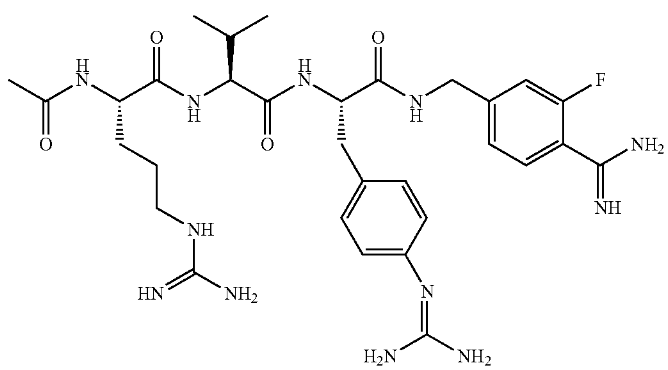 [SMILES: CC(=O)N[C@@H](CCCNC(=N)N)C(=O)N[C@H](C(=O)N[C@@H](Cc1ccc(N=C(N)N)cc1)C(=O)NCc1ccc(C(=N)N)c(F)c1)C(C)C] | 3.7 nm |
| C | 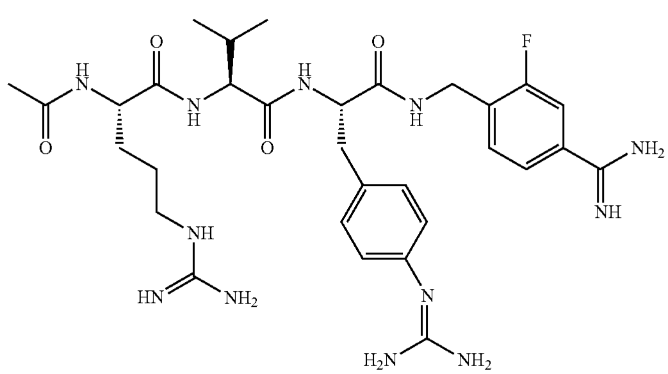 [SMILES: CC(=O)N[C@@H](CCCNC(=N)N)C(=O)N[C@H](C(=O)N[C@@H](Cc1ccc(N=C(N)N)cc1)C(=O)NCc1ccc(C(=N)N)cc1F)C(C)C] | 9 nm |

-continued

| Compound No. | Chemical Structure | IC50 against Furin |
|---|---|---|
| D | 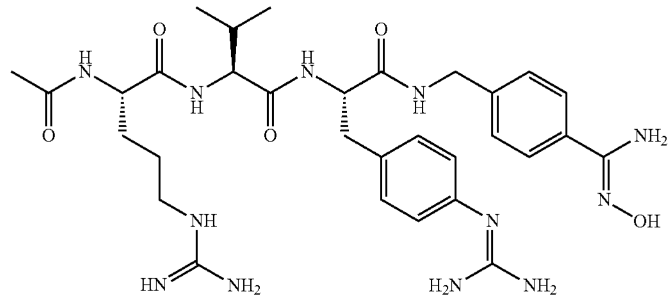 [SMILES: CC(=O)N[C@@H](CCCNC(=N)N)C(=O)N[C@H](C(=O)N[C@@H](Cc1ccc(N=C(N)N)cc1)C(=O)NCc1ccc(/C(N)=N/O)cc1)C(C)C] | 1.2 μm |
| E | 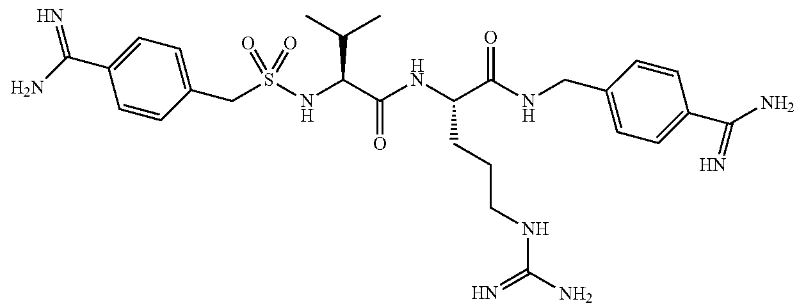 [SMILES: CC(C)[C@H](NS(=O)(=O)Cc1ccc(C(=N)N)cc1)C(=O)N[C@@H](CCCNC(=N)N)C(=O)NCc1ccc(C(=N)N)cc1] | 0.3 μm |

In certain embodiments, compounds described herein have one or more chiral centers. As such, all stereoisomers are envisioned herein. In various embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieve in any suitable manner, including by way of non-limiting example, by resolution of the racemic form by recrystallization techniques, by synthesis from optically-active starting materials, by chiral synthesis, or by chromatographic separation using a chiral stationary phase. In some embodiments, mixtures of one or more isomer is utilized as the therapeutic compound described herein. In certain embodiments, compounds described herein contains one or more chiral centers. These compounds are prepared by any means, including enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, chromatography, and the like.

In various embodiments, pharmaceutically acceptable salts described herein include, by way of non-limiting example, a nitrate, chloride, bromide, phosphate, sulfate, acetate, hexafluorophosphate, citrate, gluconate, benzoate, propionate, butyrate, sulfosalicylate, maleate, laurate, malate, fumarate, succinate, tartrate, amsonate, pamoate, p-toluenenesulfonate, mesylate and the like. Furthermore, pharmaceutically acceptable salts include, by way of non-limiting example, alkaline earth metal salts (e.g., calcium or magnesium), alkali metal salts (e.g., sodium-dependent or potassium), ammonium salts and the like. Pharmaceutically acceptable salts of the compounds of the present invention may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, $^{35}S$ or the like. In some embodiments, isotopically-labeled compounds are useful in drug and/or substrate tissue distribution studies. In some embodiments, substitution with heavier isotopes such as deuterium affords certain therapeutic advantages resulting from greater metabolic stability (for example, increased in vivo half-life or reduced dosage requirements). In some embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In some embodiments, Furin/PC inhibitors disclosed herein reduce or inhibit the binding between Furin and/or PCs and at least one of its natural binding partners (e.g., Cdc42 or Rac). In some instances, binding between Furin and/or PCs and at least one of its natural binding partners is stronger in the absence of a Furin/PC inhibitors (by e.g., 90%, 80%, 70%, 60%, 50%, 40%, 30% or 20%) than in the presence of a Furin/PC inhibitors.

In some embodiments, a Furin/PC inhibitors suitable for the methods described herein is a direct Furin/PC inhibitors. In some embodiments, a Furin/PC inhibitors suitable for the methods described herein is an indirect Furin/PC inhibitors. In some embodiments, a Furin/PC inhibitors suitable for the methods described herein decreases Furin and/or PCs activity relative to a basal level of Furin and/or PCs activity by about 1.1 fold to about 100 fold, e.g., to about 1.2 fold, 1.5 fold, 1.6 fold, 1.7 fold, 2.0 fold, 3.0 fold, 5.0 fold, 6.0 fold, 7.0 fold, 8.5 fold, 9.7 fold, 10 fold, 12 fold, 14 fold, 15 fold, 20 fold, 30 fold, 40 fold, 50 fold, 60 fold, 70 fold, 90 fold, 95 fold, or by any other amount from about 1.1 fold to about 100 fold relative to basal Furin and/or PCs activity. In some embodiments, the Furin/PC inhibitors is a reversible Furin/PC inhibitors. In other embodiments, the Furin/PC inhibitors is an irreversible Furin/PC inhibitors.

In some embodiments, a Furin/PC inhibitors used for the methods described herein has in vitro $ED_{50}$ for Furin and/or PCs activation of less than 100 µM (e.g., less than 10 µM, less than 5 µM, less than 4 µM, less than 3 µM, less than 1 µM, less than 0.8 µM, less than 0.6 µM, less than 0.5 µM, less than 0.4 µM, less than 0.3 µM, less than less than 0.2 µM, less than 0.1 µM, less than 0.08 µM, less than 0.06 µM, less than 0.05 µM, less than 0.04 µM, less than 0.03 µM, less than less than 0.02 µM, less than 0.01 µM, less than 0.0099 µM, less than 0.0098 µM, less than 0.0097 µM, less than 0.0096 µM, less than 0.0095 µM, less than 0.0094 µM, less than 0.0093 µM, less than 0.00092 µM, or less than 0.0090 µM).

In some embodiments, a Furin/PC inhibitors used for the methods described herein has in vitro $ED_{50}$ for Furin and/or PCs activation of less than 100 µM (e.g., less than 10 µM, less than 5 µM, less than 4 µM, less than 3 µM, less than 1 µM, less than 0.8 µM, less than 0.6 µM, less than 0.5 µM, less than 0.4 µM, less than 0.3 µM, less than less than 0.2 µM, less than 0.1 µM, less than 0.08 µM, less than 0.06 µM, less than 0.05 µM, less than 0.04 µM, less than 0.03 µM, less than less than 0.02 µM, less than 0.01 µM, less than 0.0099 µM, less than 0.0098 µM, less than 0.0097 µM, less than 0.0096 µM, less than 0.0095 µM, less than 0.0094 µM, less than 0.0093 µM, less than 0.00092 µM, or less than 0.0090 µM).

Synthesis and Characterization

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein. As a guide the following synthetic methods are utilized. Compounds described herein are synthesized using any suitable procedures starting from compounds that are available from commercial sources, or are prepared using procedures described herein.

Formation of Covalent Linkages by Reaction of an Electrophile with a Nucleophile The compounds described herein are modified using various electrophiles and/or nucleophiles to form new functional groups or substituents. Table below lists selected non-limiting examples of covalent linkages and precursor functional groups which yield the covalent linkages. Table A is used as guidance toward the variety of electrophiles and nucleophiles combinations available that provide covalent linkages. Precursor functional groups are shown as electrophilic groups and nucleophilic groups.

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it is necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. In some embodiments it is contemplated that each protective group be removable by a different means. Protective groups that are cleaved under totally disparate reaction conditions fulfill the requirement of differential removal.

In some embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In some embodiments carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a Pd⁰-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups are selected from:

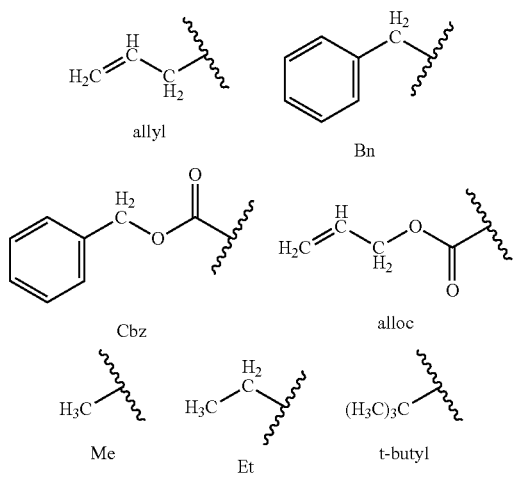

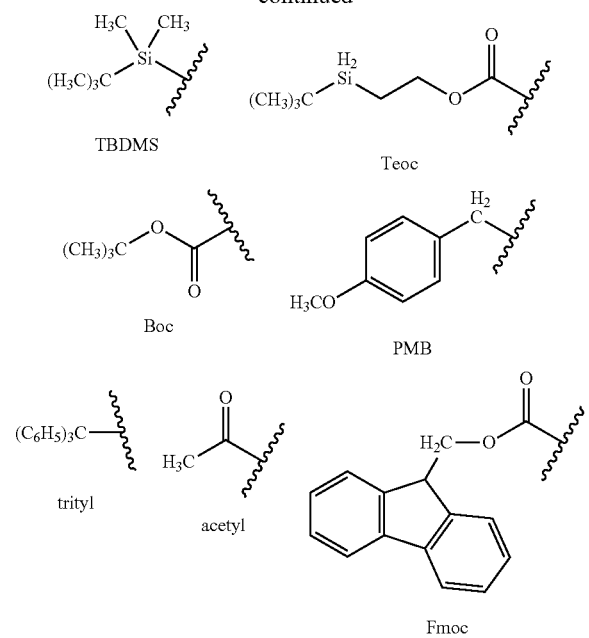

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Synthesis Example

Compound A

Compound A was prepared by a combination of solid phase and solution synthesis. Briefly, the N-acylated segment P2-P4 protected in P2 and P4 positions, after weak acidic cleavage from the 2-chloro-tritylchloride resin was coupled to unprotected 4-amidinobenzylamine and derivatives, followed by side chains deprotection. All the final compounds were purified by both preparative and semipreparative reverse phase HPLC, lyophilized and obtained as TFA or HCl salts.

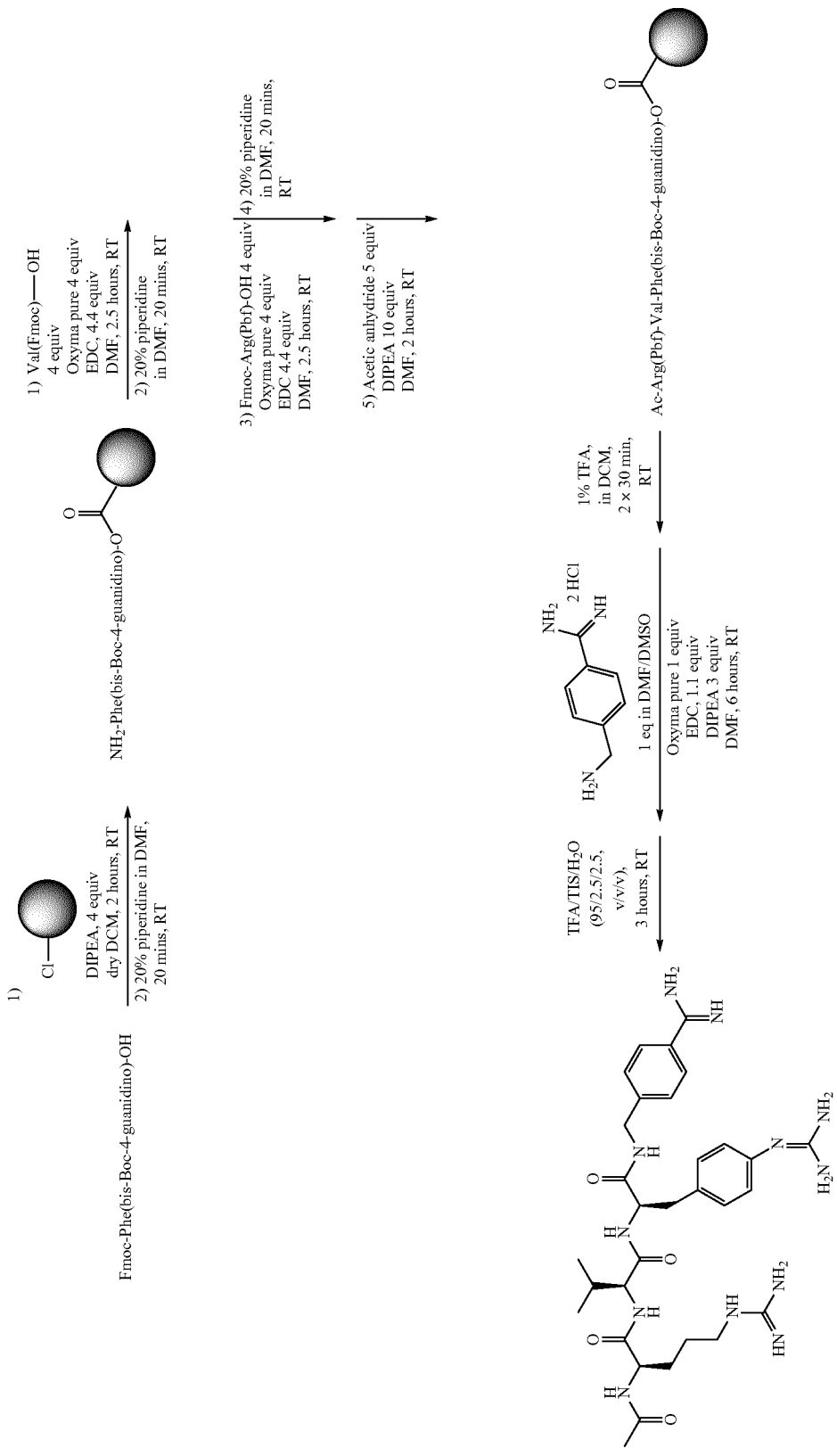

Purity of all compounds was obtained by analytical HPLC on a Breeze system from Waters Co. using a 5 μm, 4.6×150 mm symmetry reverse phase column with a linear gradient of acetonitrile containing 0.1% TFA at a flow rate of 1 mL/min and by $^1$H NMR spectra recorded on a Bruker 600 MHz instrument.

Figure 1:
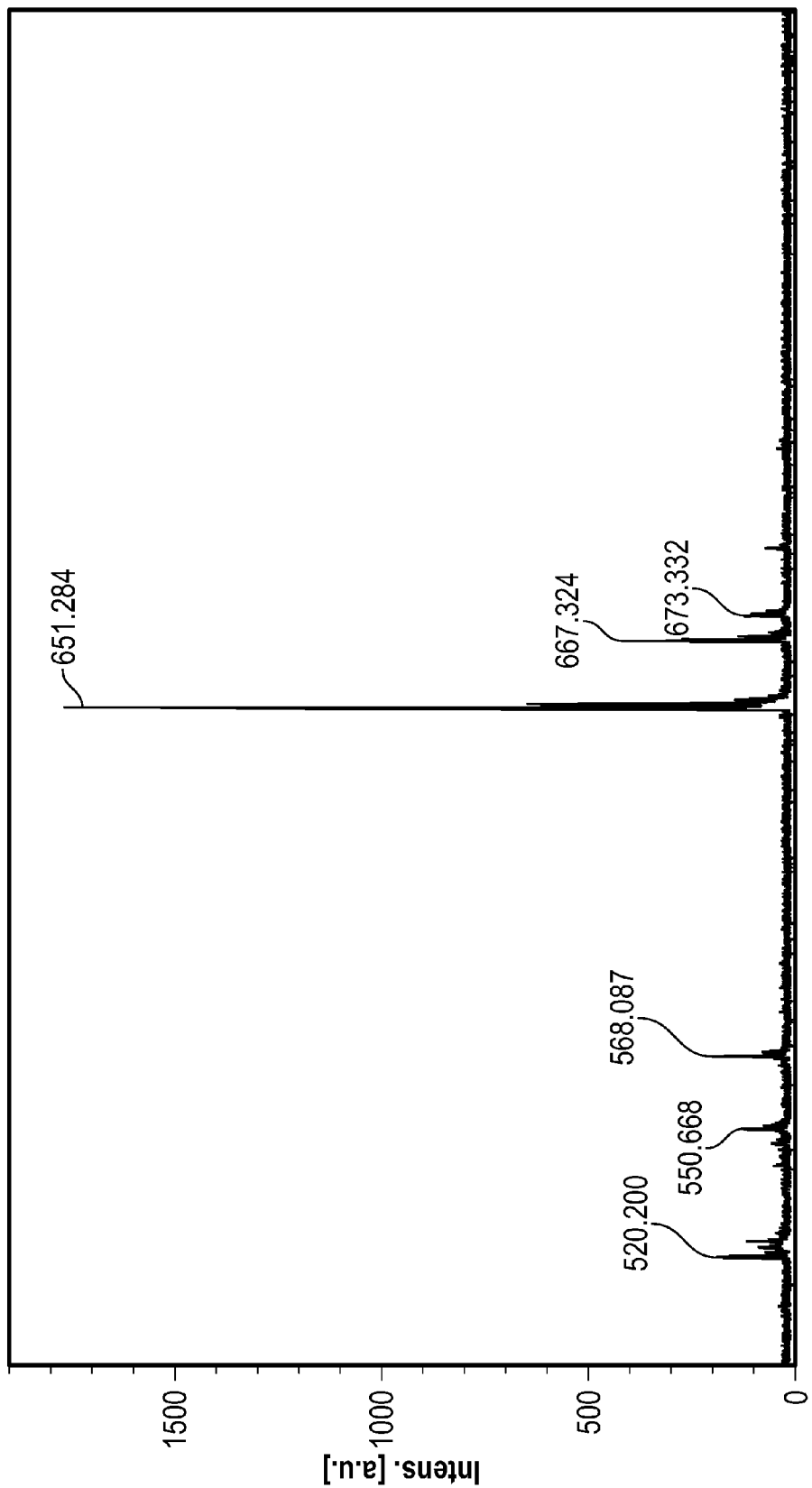
FIG. 1 exemplifies the HPLC profile of Compound A.
Figure 2:
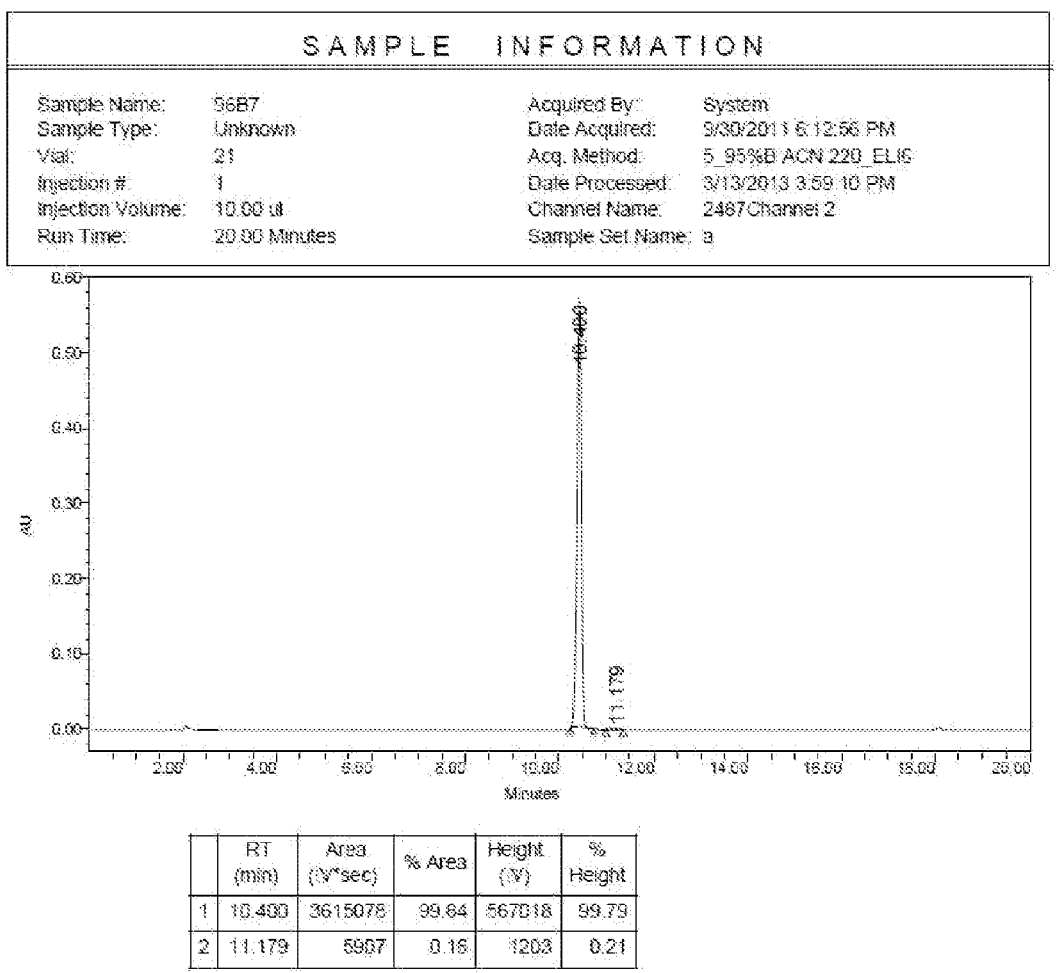
FIG. 2 exemplifies the MS profile of Compound A 2.

The HPLC and MS profile of Compound A is presented in FIG. 1 and FIG. 2.

Figure 3:
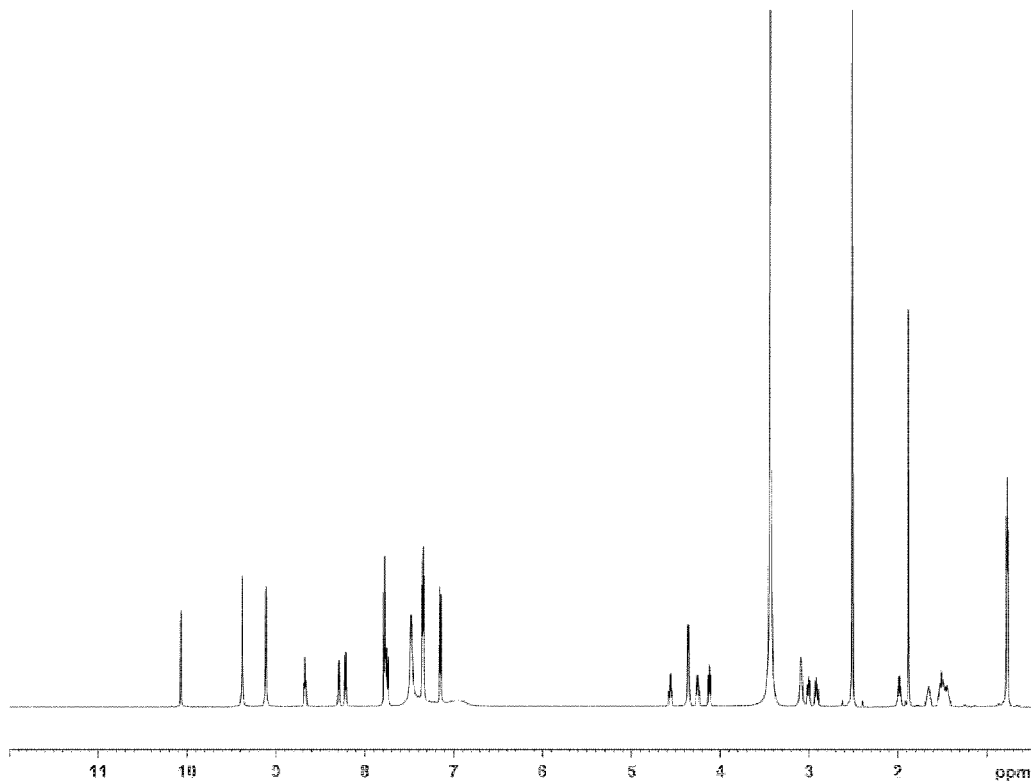
FIG. 3 exemplifies the $^1$H NMR spectrum of Compound A in DMSO-d6.

$^1$H NMR spectrum of Compound A in DMSO-d6 is presented in FIG. 3.

Compound B:

Compound B was prepared similar to Compound A according to the reaction scheme below. All the final compounds were purified by both preparative and semipreparative reverse phase HPLC, lyophilized and obtained as TFA or HCl salts.

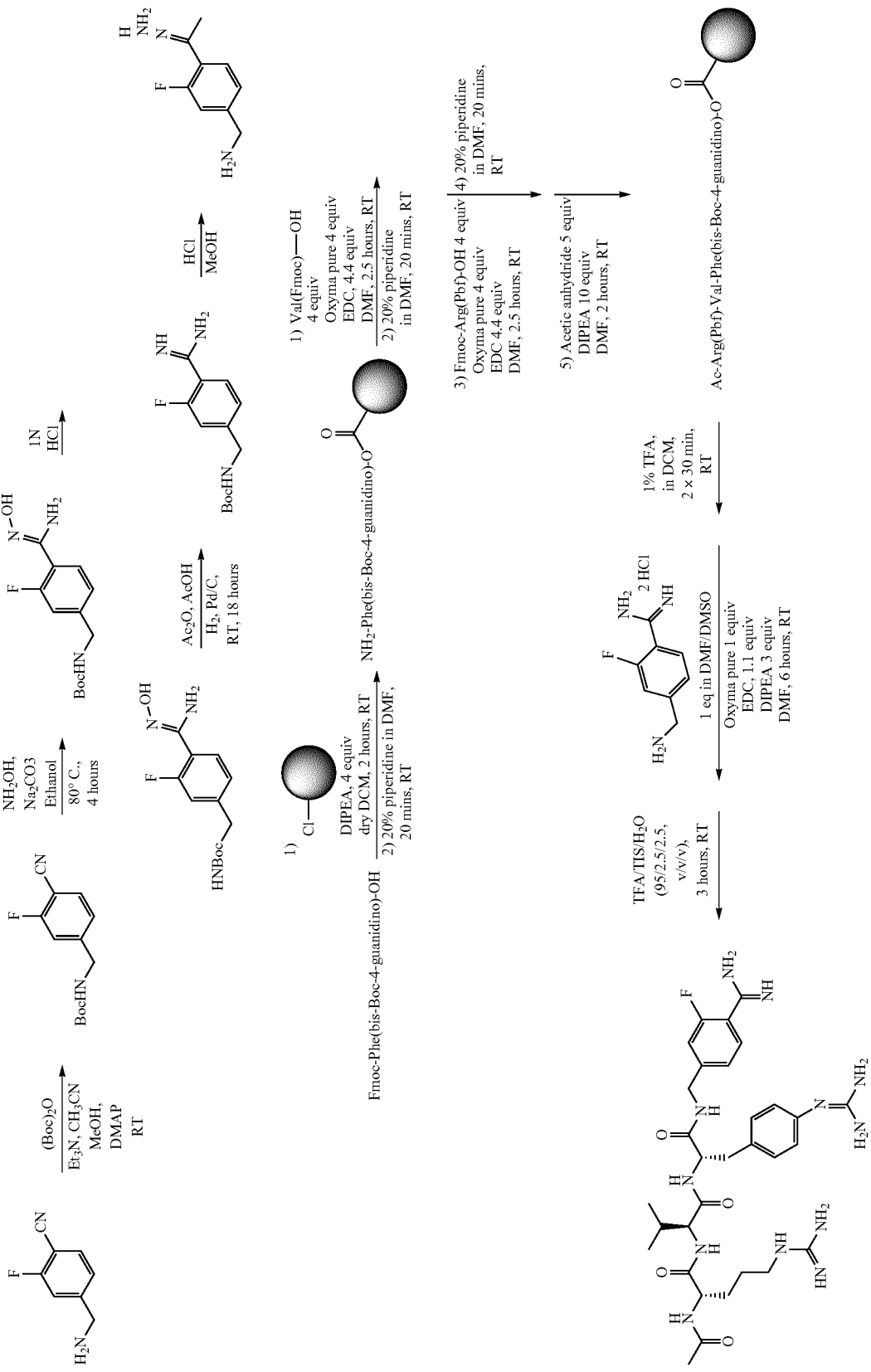

Figure 4:
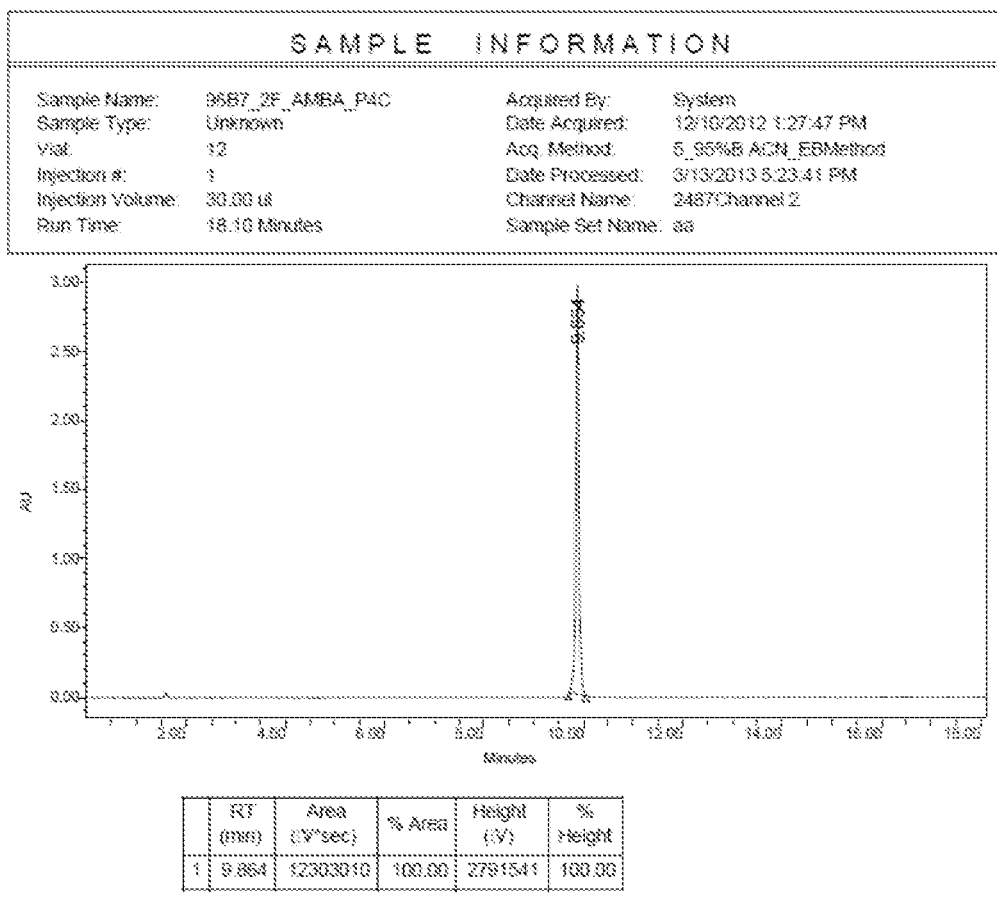
FIG. 4 exemplifies the HPLC profile Compound B.

HPLC of Compound B is presented in FIG. 4.

Figure 5:
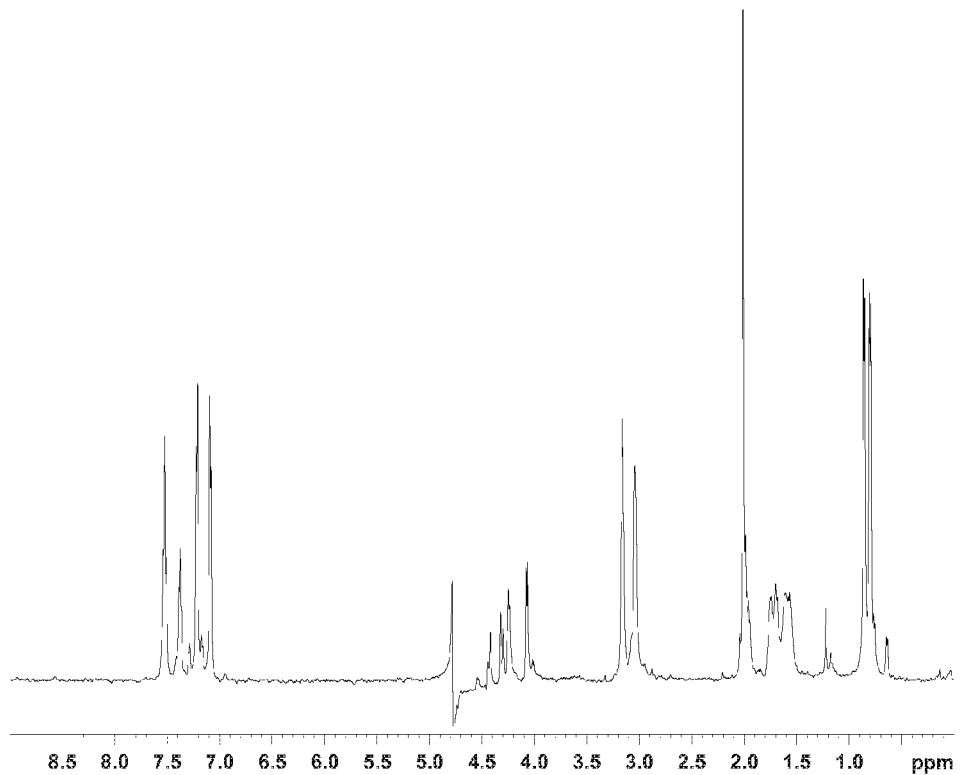
FIG. 5 exemplifies the $^1$H NMR spectrum of Compound B in deuterated PBS.

$^1$H NMR spectrum of Compound B in deuterated PBS is presented in FIG. 5.

Compound D

Compound D was prepared similar to Compound A according to the reaction scheme below. All the final compounds were purified by both preparative and semipreparative reverse phase HPLC, lyophilized and obtained as TFA or HCl salts.

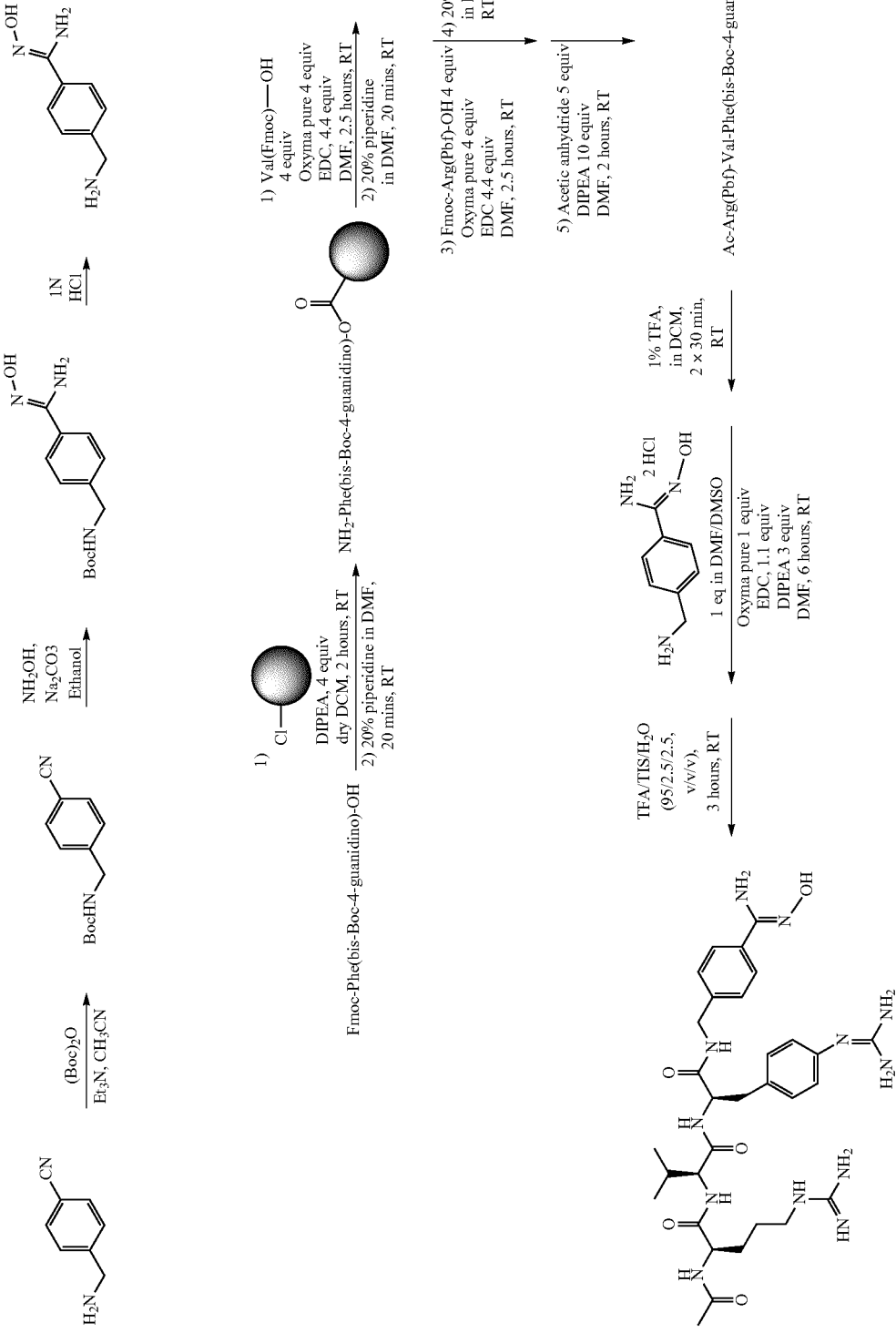

MS (MALDI) and HPLC profile of Compound D is presented in FIG. 6 and FIG. 7.

$^1$H NMR spectrum of Compound D in deuterated PBS is presented in FIG. 8.

Compound E

Compound E was prepared by a combination of solid phase and solution synthesis. Briefly, the segment P2-P4 protected in P2, after weak acidic cleavage from the 2-chloro-tritylchloride resin was coupled to unprotected 4-amidinobenzylamine, followed by final side chain deprotection. The final products were purified by both preparative and semipreparative reversed phase HPLC and obtained Compound E as lyophilized powder.

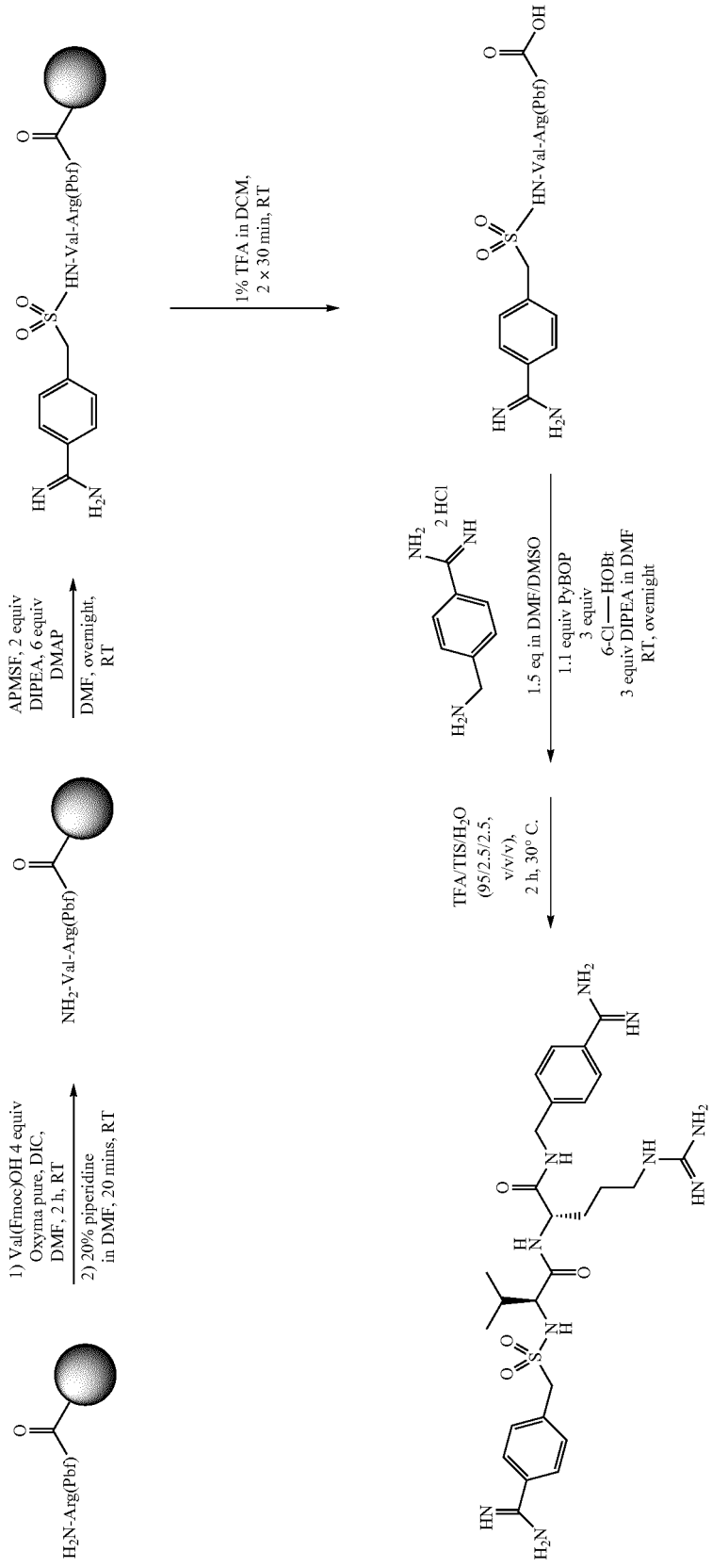

Purity of Compound E was obtained by analytical HPLC on a Breeze system from Waters Co. using a 5 μm, 4.6×150 mm symmetry reverse phase column with a linear gradient of acetonitrile containing 0.1% TFA at a flow rate of 1 mL/min and by $^1$H NMR spectra recorded on a Bruker 600 MHz instrument HPLC and MS profile of Compound E is presented in FIG. 9 and FIG. 10.

$^1$H NMR spectrum of Compound E in DMSO-d6 is presented in FIG. 11.

Other compounds according to the present disclosure can be similarly prepared in light of the present disclosure and examples provided herein.

Bioassay Example

Compound A

Macrophage Cytotoxicity Assay.

RAW 264.7 Murine monocyte macrophages ($4.5 \times 10^4$ cells/well) were plated into 96-well tissue culture plates in Hyclone DMEM (4500 mg/L Glucose, 110 g/L Sodium Pyruvate) supplemented with 5% fetal bovine serum, 2 mM Glutamax (Invitrogen, Carlsbad, Calif.), 1% penicillin/streptomycin (Omega Scientific). Cells were cultured overnight at 37° C. in a humidified incubator containing 5% $CO_2$. They were replenished with fresh serum-free medium (0.1 ml/well) and exposed to a pre-incubated solution of test compounds (increasing concentrations from 0.015 to 33.3 uM), $PA_{83}$ (500 ng/mL) and LF (37.5 ng/mL). The analyzed inhibitors were dissolved in DMSO reaching a final DMSO concentration of 1%. Controls included untreated cells and LF/PA-only treated cells. After incubation for 3.5 hours at 37° C., cell viability was assessed using ATPlite assay from Perkin Elmer (Waltham, Mass.). Each datum point represents triplicates of each concentration in one experiment. Viability was normalized to control cells which were treated with the vehicle, DMSO. Biochemical assay dose response for Compound A is presented in FIG. 12.

Dengue viral replication assay. Primary cytopathic effect (CPE) reduction assay. Four-concentration CPE inhibition assays are performed. Confluent or near-confluent cell culture monolayers in 96-well disposable microplates are prepared. Cells are maintained in MEM or DMEM supplemented with FBS as required for each cell line. For antiviral assays the same medium is used but with FBS reduced to 2% or less and supplemented with 50 μg/ml gentamicin. The test compound is prepared at four log 10 final concentrations, usually 0.1, 1.0, 10, and 100 μg/ml or μM. The virus control and cell control wells are on every microplate. In parallel, a known active drug is tested as a positive control drug using the same method as is applied for test compounds. The positive control is tested with each test run. The assay is set up by first removing growth media from the 96-well plates of cells. Then the test compound is applied in 0.1 ml volume to wells at 2× concentration. Virus, normally at <100 50% cell culture infectious doses (CCID50) in 0.1 ml volume, is placed in those wells designated for virus infection. Medium devoid of virus is placed in toxicity control wells and cell control wells. Virus control wells are treated similarly with virus. Plates are incubated at 37° C. with 5% CO2 until maximum CPE is observed in virus control wells. The plates are then stained with 0.011% neutral red for approximately two hours at 37° C. in a 5% $CO_2$ incubator. The neutral red medium is removed by complete aspiration, and the cells may be rinsed 1× with phosphate buffered solution (PBS) to remove residual dye. The PBS is completely removed and the incorporated neutral red is eluted with 50% Sorensen's citrate buffer/50% ethanol (pH 4.2) for at least 30 minutes. Neutral red dye penetrates into living cells, thus, the more intense the red color, the larger the number of viable cells present in the wells. The dye content in each well is quantified using a 96-well spectrophotometer at 540 nm wavelength. The dye content in each set of wells is converted to a percentage of dye present in untreated control wells using a Microsoft Excel computer-based spreadsheet. The 50% effective (EC50, virus-inhibitory) concentrations and 50% cytotoxic (CC50, cell-inhibitory) concentrations are then calculated by linear regression analysis. The quotient of CC50 divided by EC50 gives the selectivity index (SI) value.

Secondary CPE/Virus yield reduction (VYR) assay. This assay involves similar methodology to what is described in the previous paragraphs using 96-well microplates of cells. The differences are noted in this section. Eight half-log 10 concentrations of inhibitor are tested for antiviral activity and cytotoxicity. After sufficient virus replication occurs, a sample of supernatant is taken from each infected well (three replicate wells are pooled) and held for the VYR portion of this test, if needed. Alternately, a separate plate may be prepared and the plate may be frozen for the VYR assay. After maximum CPE is observed, the viable plates are stained with neutral red dye. The incorporated dye content is quantified as described above. The data generated from this portion of the test are neutral red EC50, CC50, and SI values. Compounds observed to be active above are further evaluated by VYR assay. The VYR test is a direct determination of how much the test compound inhibits virus replication. Virus that was replicated in the presence of test compound is titrated and compared to virus from untreated, infected controls. Titration of pooled viral samples (collected as described above) is performed by endpoint dilution. This is accomplished by titrating log 10 dilutions of virus using 3 or 4 microwells per dilution on fresh monolayers of cells by endpoint dilution. Wells are scored for presence or absence of virus after distinct CPE (measured by neutral red uptake) is observed. Plotting the log 10 of the inhibitor concentration versus log 10 of virus produced at each concentration allows calculation of the 90% (one log 10) effective concentration by linear regression. Dividing EC90 by the CC50 obtained in part 1 of the assay gives the SI value for this test. Compound A has a cellular activity against Dengue (EC90) of 14 μm.

Compound B and Compound C

Macrophage cytotoxicity assay. RAW 264.7 Murine monocyte macrophages ($4.5 \times 10^4$ cells/well) were plated into 96-well tissue culture plates in Hyclone DMEM (4500 mg/L Glucose, 110 g/L Sodium Pyruvate) supplemented with 5% fetal bovine serum, 2 mM Glutamax (Invitrogen, Carlsbad, Calif.), 1% penicillin/streptomycin (Omega Scientific). Cells were cultured overnight at 37° C. in a humidified incubator containing 5% $CO_2$. They were replenished with fresh serum-free medium (0.1 ml/well) and exposed to a pre-incubated solution of test compounds (increasing concentrations from 0.015 to 33.3 uM), $PA_{83}$ (500 ng/mL) and LF (37.5 ng/mL). The analyzed inhibitors were dissolved in DMSO reaching a final DMSO concentration of 1%. Controls included untreated cells and LF/PA-only treated cells. After incubation for 3.5 hours at 37° C., cell viability was assessed using ATPlite assay from Perkin Elmer (Waltham, Mass.). Each datum point represents triplicates of each concentration in one experiment. Viability was normalized to control cells which were treated with the vehicle, DMSO.

Biochemical assay dose response for Compound B and Compound C (with one chiral center unresolved) is presented in FIG. 13.

Compound E

Macrophage cytotoxicity. RAW 264.7 Murine monocyte macrophages ($4.5 \times 10^4$ cells/well) were plated into 96-well tissue culture plates in Hyclone DMEM (4500 mg/L Glucose, 110 g/L Sodium Pyruvate) supplemented with 5% fetal bovine serum, 2 mM Glutamax (Invitrogen, Carlsbad, Calif.), 1% penicillin/streptomycin (Omega Scientific). Cells were cultured overnight at 37° C. in a humidified incubator containing 5% $CO_2$. They were replenished with fresh serum-free medium (0.1 ml/well) and exposed to a pre-incubated solution of test compounds (increasing concentrations from 0.015 to 33.3 uM), $PA_{83}$ (500 ng/mL) and LF (37.5 ng/mL). The analyzed inhibitors were dissolved in DMSO reaching a final DMSO concentration of 1%. Controls included untreated cells and LF/PA-only treated cells. After incubation for 3.5 hours at 37° C., cell viability was assessed using ATPlite assay from Perkin Elmer (Waltham, Mass.). Each datum point represents triplicates of each concentration in one experiment. Viability was normalized to control cells which were treated with the vehicle, DMSO.

Purification of soluble furin. Furin-overexpressing MDCK cells were grown using 15 cm plates (Falcon) in DMEM/High modified synthetic media (Thermo Scientific) supplemented with Gentamicin (10 µg/ml). Each two days the medium was collected. Cells were replenished with fresh medium. To remove cell debris, the collected samples were spun at 3000×g and the supernatant fraction was filtered through a 0.22 µm filter (Corning) and then 100-fold concentrated using a Pellicon XL Biomax 10 concentrator (Millipore). Furin was isolated from the concentrated medium samples using $Ni^{2+}$-chelating chromatography on a HiTrap Chelating HP 1.6×2.5 cm column (Amersham Biosciences) equilibrated with 20 mM Tris-HCl buffer, pH 8.0, containing 1M NaCl. To remove the impurities, the column was washed with 50 ml of the same buffer containing 25 mM imidazole. Furin was eluted using 500 mM imidazole. The purified fractions were pooled, concentrated using an Amicon Ultra 50K-cutoff membrane (Millipore), dialyzed against PBS and stored at −80° C. According to SDS-PAGE followed by Coomassie staining of the gel, Western blotting and enzyme activity assays the purity of the isolated furin samples was >95%. The typical yield of purified furin was 0.8-1 mg/liter of cell culture medium. Specific activity of purified furin was >120 units where one unit is the amount of furin that will cleave 1.0 pmol methyl-coumaryl-7-amide (AMC) from the Pyr-Arg-Thr-Lys-Arg-methyl-coumaryl-7-amide (Pyr-RTKR-AMC) substrate per min at ambient temperature, pH 7.5.

Enzymatic assay. Furin activity was measured in triplicate in wells of a 96-well plate in 0.2 ml 50 mM HEPES, pH 7.5, containing 1 mM $CaCl_2$, 0.005% Brij-35 and 20% glycerol. Pyr-RTKR-AMC (25 µM) was used as a substrate. The concentration of furin in the reactions was 50 nM. The steady-state rate of substrate hydrolysis was monitored continuously ($\lambda_{ex}$=360 nm and $\lambda_{em}$=465 nm) at 37° C. using a Spectramax Gemini EM fluorescent spectrophotometer (Molecular Devices).

Determination of the $IC_{50}$ values of the compounds. Furin (50 nM) was preincubated for 30 min at 20° C. with increasing concentrations of the individual compounds in 0.1 ml of 50 mM HEPES, pH 7.5, containing 1 mM $CaCl_2$, 20% glycerol and 0.005% Brij 35. The Pyr-RTKR-AMC substrate (25 λM) was added in 0.1 ml of the same buffer. Reaction velocity was monitored continuously at $\lambda_{ex}$=360 nm and $\lambda_{em}$=465 nm on a Spectramax Gemini EM fluorescence spectrophotometer. All assays were performed in triplicate in wells of a 96-well plate. $IC_{50}$ values were calculated by determining the concentrations of the compounds needed to inhibit 50% of the furin activity against Pyr-RTKR-AMC substrate. GraphPad Prism was used as fitting software.

Biochemical assay dose response for Compound E is presented in FIG. 14.

Diseases and Conditions

Viral and/or Infectious Diseases

Disclosed herein, in certain embodiments, are methods of neutralizing an exotoxin in a subject in need thereof comprising administering a Furin/PC inhibitors disclosed herein. In some embodiments, the exotoxin is anthrax toxin, pseudomonas exotoxin A, Shiga toxin, diphtheria toxin, tetanus and botulism neurotoxins, and combinations thereof. In addition, some Furin/PC inhibitors, including those disclosed herein, are capable of neutralizing virulence of bacteria carrying those exotoxin.

PCs, including furin, are involved in many pathogenic states as they process to maturity membrane fusion proteins and toxins of a variety of both bacteria and viruses, including anthrax and botulinum toxins, influenza A H5N1 (bird flu), flaviviruses, Marburg, influenza virus, human immunodeficiency virus 1, Ebola, measles, cytomegalovirus, and flaviviruses (Dengue, Yellow fever, West Nile, Japanese encephalitis and multiple additional related flaviviruses) and parasitic nematodes.

After processing by furin and the subsequent endocytic internalization in the complex with the respective cell surface receptor followed by acidification of the endosomal compartment, the processed, partially denatured, infectious proteins expose their membrane-penetrating peptide region and escape into the cytoplasm. The intact toxins and viral proteins, however, are incapable of accomplishing these processes, because they cannot penetrate the membrane and escape into the cytoplasm.

Cancer

Disclosed herein, in certain embodiments, are methods of treating cancer in a subject in need thereof comprising administering a Furin/PC inhibitors disclosed herein. In some embodiments, the cancer is lung cancer, colon cancer, squamous cell carcinoma, SCC Head and neck, skin cancer, astrocytoma, or any combinations thereof.

Furin and other PC family members (furin/PCs) activate proteins vital to proper physiological functioning, including growth factors and hormones, receptors, plasma proteins, and matrix metalloproteases (MMPs). Some of the PC substrates, such as growth factors and their receptors, matrix metalloproteinases and adhesion molecules, are involved in the neoplastic transformation, proliferation, invasion and metastasis formation. In certain instances, the expression and activity of furin/PC are necessary for processing substrates important for cell transformation and tumor progression, metastasis, and angiogenesis. Furin processing of the remodeling protease membrane type-1 matrix metalloproteinase (MT1-MMP) enhances cellular motility and invasiveness, contributing to aggression and metastatic potential cancer cells. In certain instances, overexpression and activity of furin/PC exacerbate a cancer phenotype. In certain instances, inhibition of furin/PC activity decreases or nullifies furin/PC-mediated effects on cancers.

The expression of furin is higher in squamous cell carcinomas and adenocarcinomas, than in small-cell lung carcinomas (SCLCs). Opposite results were found for PC1 and PC2 expression where mRNAs are absent in normal lung epithelium and non-small cell lung cancers but over-expressed in multiple lung cancer cell lines.

The expression of PC1 and PC2 is altered in liver colorectal metastasis when compared to a normal liver. Moreover, PC2 overexpression was found to correlate with the expression of its specific binding protein 7B2. Inhibition of PC decreased proliferation and invasive ability in HT-29 human colon carcinoma cells and tumorigenicity in xenografts. This effect was linked to inhibition of IGF1R processing by furin and PC5 downregulation.

The up-regulation of VEGF-C by furin is associated with squamous carcinogenesis development. Further, furin inhibition reduces of invasiveness and tumorigenicity in a HNSCC model due to decrease in processing of TGFβ and MT1-MMP.

In human primary melanoma cells, inhibition of PC leads to a decrease in invasiveness which correlates with the inability of the cells to process PC substrates such as pro-IGF1R, pro-PDGFA or pro-MMPs. Moreover, inhibition of PACE4 in skin carcinoma cells, characterized by high PACE4 activity, causes a decrease in both cell proliferation in vitro and tumor development in vivo via disruption of IGF1R signaling.

Furin is expressed in primary glial cell cultures and elevated expression is seen in tumorigenic astrocytoma cell lines. Inhibition of furin by α1-PDX results in a decrease in cell growth, an inhibition of tumorigenicity and invasion caused by inability of the cells to activate MT1-MMP and, consequently, to activate MMP-2. Furthermore, in vivo invasiveness is also reduced.

"Cancer" includes any malignant growth or tumor caused by abnormal and uncontrolled cell division. "Cancer" includes solid tumors and non-solid tumors. Examples of cancers include CML, CNS cancer, Hodgkin's Disease, NSCLC, a T-cell lymphoma, a B-cell lymphoma, adenocarcinoma, adenocarcinoma, bladder cancer, bone cancer, brain cancer, brain stem glioma, breast cancer, cancer of the adrenal gland, cancer of the anal region, cancer of the bladder, cancer of the endocrine system, cancer of the esophagus, cancer of the parathyroid gland, cancer of the penis, cancer of the small intestine, cancer of the thyroid gland, cancer of the urethra, carcinoma of the cervix, carcinoma of the endometrium, carcinoma of the fallopian tubes, carcinoma of the renal pelvis, carcinoma of the vagina, carcinoma of the vulva, colon cancer, cutaneous or intraocular melanoma, gastric cancer, gastrointestinal stromal tumors, gastrointestinal stromal tumors, glioblastoma, head and neck cancer, hepatocellular cancer, kidney cancer, leukemia, lung cancer, lymphocytic lymphomas, lymphoma, melanoma, meningiomas, myeloma, neurofibromatosis, renal cell carcinoma, ovarian cancer, pancreatic cancer, pituitary adenoma, primary CNS lymphoma, prostate cancer, rectal cancer, renal cell carcinoma, sarcoma of soft tissue, spinal axis tumors, spontaneous schwannomas, stomach cancer, uterine cancer, or any combinations thereof.

Inflammatory and Autoimmune Disorders

Disclosed herein, in certain embodiments, are methods of treating an inflammatory or autoimmune disorder in a subject in need thereof comprising administering a furin/PC inhibitor disclosed herein. In some embodiments, the inflammatory or autoimmune disorder is Alzheimer's Disease, arthritis, atherosclerosis, or any combinations thereof.

The novel transmembrane aspartic protease BACE (for Beta-site APP CleavingEnzyme) is the β-secretase that cleaves amyloid precursor protein to initiate β-amyloid formation. As such, BACE is a prime therapeutic target for the treatment of Alzheimer's disease. BACE, like other aspartic proteases, has a propeptide domain that is removed to form the mature enzyme. BACE propeptide cleavage occurs at the sequence RLPR↓E. BACE and furin co-localize within the Golgi apparatus, and propeptide cleavage is inhibited by brefeldin A and monensin, drugs that disrupt trafficking through the Golgi. Treatment of cells with the calcium ionophore A23187, leading to inhibition of calcium-dependent proteases including furin, or transfection with the α1-antitrypsin variant α1-PDX, a potent furin inhibitor, dramatically reduces cleavage of the BACE propeptide. Moreover, the BACE propeptide is not processed in the furin-deficient LoVo cell line; however, processing is restored upon furin transfection. Finally, in vitro digestion of recombinant soluble BACE with recombinant furin results in complete cleavage only at the established E46 site.

In some embodiments, the autoimmune or inflammatory disorder is: Acute disseminated encephalomyelitis; Addison's disease; Ankylosing spondylitis; Antiphospholipid antibody syndrome; Autoimmune hemolytic anemia; Autoimmune hepatitis; Autoimmune inner ear disease; Bullous pemphigoid; Chagas disease; Chronic obstructive pulmonary disease; Coeliac disease; Dermatomyositis; Diabetes mellitus type 1; Diabetes mellitus type 2; Endometriosis; Goodpasture's syndrome; Graves' disease; Guillain-Barré syndrome; Hashimoto's disease; Idiopathic thrombocytopenic purpura; Interstitial cystitis; Systemic lupus erythematosus (SLE); Metabolic syndrome, Multiple sclerosis; Myasthenia gravis; Myocarditis, Narcolepsy; Obesity; Pemphigus Vulgaris; Pernicious anaemia; Polymyositis; Primary biliary cirrhosis; Rheumatoid arthritis; Schizophrenia; Scleroderma; Sjögren's syndrome; Vasculitis; Vitiligo; Wegener's granulomatosis; Allergic rhinitis; Ulcerative colitis; Crohn's disorder; Collagenous colitis; Lymphocytic colitis; Ischaemic colitis; Diversion colitis; Behçet's syndrome; Infective colitis; Indeterminate colitis; Inflammatory liver disorder, Endotoxin shock, Rheumatoid spondylitis, Ankylosing spondylitis, Gouty arthritis, Polymyalgia rheumatica, Alzheimer's disorder, Parkinson's disorder, Epilepsy, AIDS dementia, Asthma, Adult respiratory distress syndrome, Bronchitis, Cystic fibrosis, Acute leukocyte-mediated lung injury, Distal proctitis, Wegener's granulomatosis, Fibromyalgia, Bronchitis, Cystic fibrosis, Uveitis, Conjunctivitis, Psoriasis, Eczema, Dermatitis, Smooth muscle proliferation disorders, Meningitis, Shingles, Encephalitis, Nephritis, Tuberculosis, Retinitis, Atopic dermatitis, Pancreatitis, Periodontal gingivitis, Coagulative Necrosis, Liquefactive Necrosis, Fibrinoid Necrosis, Hyperacute transplant rejection, Acute transplant rejection, Chronic transplant rejection, Acute graft-versus-host disease, Chronic graft-versus-host disease, or combinations thereof.

Pharmaceutical Compositions and Methods of Administration

Provided herein, in certain embodiments, are pharmaceutical compositions comprising a therapeutically effective amount of a Furin/PC inhibitor disclosed herein and a pharmaceutically-acceptable excipient.

Pharmaceutical compositions are formulated using one or more physiologically acceptable excipients. Proper formulation is dependent upon the route of administration chosen. A summary of pharmaceutical compositions is found, for example, in Remington: The Science and Practice of Pharmacy, Nineteenth Ed (Ea hston, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

In some embodiments, the pharmaceutically compositions further comprise a pharmaceutically acceptable diluent(s), excipient(s), or carrier(s). In addition, the Furin/PC inhibitors is optionally administered as pharmaceutical compositions in which it is mixed with other active ingredients, as in combination therapy. In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

The pharmaceutical formulations described herein are optionally administered to an individual by any suitable administration route, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the pharmaceutical compositions comprise at least one Furin/PC inhibitor disclosed herein, as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these Furin/PC inhibitors having the same type of activity. In some embodiments, Furin/PC inhibitors disclosed herein exist as tautomers. All tautomers are included within the scope of the Furin/PC inhibitors disclosed herein. Additionally, the Furin/PC inhibitors exist in unsolvated as well as solvated forms with pharmaceutically acceptable solvents such as water, ethanol, and the like. The solvated forms of the Furin/PC inhibitors presented herein are also considered to be disclosed herein.

"Carrier materials" include any commonly used excipients in pharmaceutics and should be selected on the basis of compatibility with a Furin/PC inhibitor disclosed herein and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

Moreover, the pharmaceutical compositions described herein are formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

In some embodiments, the pharmaceutical compositions disclosed herein are solid drug dispersions. A solid dispersion is a dispersion of one or more active ingredients in an inert carrier or matrix at solid state prepared by the melting (or fusion), solvent, or melting-solvent methods (Chiou and Riegelman, Journal of Pharmaceutical Sciences, 60, 1281 (1971)). The dispersion of one or more active agents in a solid diluent is achieved without mechanical mixing. Solid dispersions are also called solid-state dispersions.

In some embodiments, the pharmaceutical compositions disclosed herein are spray dried dispersions (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion. In some embodiments, such amorphous dispersions are filled in capsules and/or constituted into oral powders for reconstitution. Solubility of an SDD comprising a drug is higher than the solubility of a crystalline form of a drug or a non-SDD amorphous form of a drug.

Pharmaceutical preparations for oral use are optionally obtained by mixing one or more solid excipients with a Furin/PC inhibitor disclosed herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross linked croscarmellose sodium, polyvinylpyrrolidone, agar, or alginic acid or a salt thereof such as sodium alginate.

Dragee cores are provided with suitable coatings. For this purpose, concentrated sugar solutions are generally used, which optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments are optionally added to the tablets or dragee coatings for identification.

In some embodiments, a composition disclosed herein is formulated as a solid dosage form. In some embodiments, a Furin/PC inhibitor disclosed here is a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In some embodiments, a Furin/PC inhibitor disclosed here is a capsule. In some embodiments, a Furin/PC inhibitor disclosed here is a powder.

In some embodiments, a pharmaceutical composition disclosed herein is a microencapsulated formulation. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary microencapsulation materials useful for delaying the release of the formulations including a Furin/PC inhibitors, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS)

and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S 100, Eudragit® RD 100, Eudragit® E100, Eudragite® L12.5, Eudragit® 512.5, Eudragit® NE30D, and Eudragit® NE 40D, cellulose acetate phthalate, sepifilms such as mixtures of HPMC and stearic acid, cyclodextrins, and mixtures of these materials.

In some embodiments, a pharmaceutical composition disclosed herein is formulated to provide controlled release of a Furin/PC inhibitor disclosed herein. Controlled release profiles include, for example, sustained release, prolonged release, pulsatile release, and delayed release profiles. In contrast to immediate release compositions, controlled release compositions allow delivery of an agent to an individual over an extended period of time according to a predetermined profile. Such release rates provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, a composition disclosed herein is formulated as a pulsatile dosage form.

In some embodiments, a composition disclosed herein is formulated as a liquid dosage form. In some embodiments, a pharmaceutical composition disclosed herein is an aqueous suspension selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition, the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, a pharmaceutical formulation described herein is a self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960, 563.

In some embodiments, a pharmaceutical composition described herein is formulated for nasal administration. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present.

In some embodiments, a pharmaceutical compositions disclosed herein is an aerosol, a mist or a powder. In some embodiments, a pharmaceutical composition described herein is delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit is determined by providing a valve to deliver a metered amount. Capsules and cartridges of, such as, by way of example only, gelatin for use in an inhaler or insufflator are formulated containing a powder mix of a Furin/PC inhibitor disclosed herein and a suitable powder base such as lactose or starch.

In some embodiments, a pharmaceutical composition described herein is formulated for buccal administration. Buccal formulations that include a Furin/PC inhibitor disclosed herein include, but are not limited to, U.S. Pat. Nos. 4,229,447, 4,596,795, 4,755,386, and 5,739,136. In addition, the buccal dosage forms described herein optionally further include a bioerodible (hydrolysable) polymeric carrier that also serves to adhere the dosage form to the buccal mucosa. The buccal dosage form is fabricated so as to erode gradually over a predetermined time period, wherein the delivery of the Furin/PC inhibitors, is provided essentially throughout. Buccal drug delivery avoids the disadvantages encountered with oral drug administration, e.g., slow absorption, degradation of the active agent by fluids present in the gastrointestinal tract and/or first-pass inactivation in the liver. The bioerodible (hydrolysable) polymeric carrier generally comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components also be incorporated into the buccal dosage forms described herein include, but are not limited to, disintegrants, diluents, binders, lubricants, flavoring, colorants, preservatives, and the like. For buccal or sublingual administration, the compositions optionally take the form of tablets, lozenges, or gels formulated in a conventional manner. By way of example, Examples 26c and 26d describe sublingual formulations.

In some embodiments, a pharmaceutical composition described herein is formulated for transdermal administration.

In some embodiments, a transdermal formulation described herein comprises: (1) a Furin/PC inhibitor disclosed herein; (2) a penetration enhancer; and (3) an aqueous adjuvant. In addition, transdermal formulations include components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein maintain a saturated or supersaturated state to promote diffusion into the skin.

In some embodiments, formulations suitable for transdermal administration of a Furin/PC inhibitor disclosed herein employ transdermal delivery devices and transdermal delivery patches and are lipophilic emulsions or buffered, aqueous solutions, dissolved and/or dispersed in a polymer or an adhesive. Such patches are optionally constructed for continuous, pulsatile, or on demand delivery of pharmaceutical agents. Still further, transdermal delivery of a Furin/PC inhibitor disclosed herein is optionally accomplished by means of iontophoretic patches and the like. Additionally, transdermal patches provide controlled delivery of a Furin/PC inhibitor. The rate of absorption is optionally slowed by using rate-controlling membranes or by trapping a Furin/PC inhibitor within a polymer matrix or gel. Conversely, absorption enhancers are used to increase absorption. An absorption enhancer or carrier includes absorbable pharmaceutically acceptable solvents to assist passage through the skin. For example, transdermal devices are in the form of a bandage comprising a backing member, a reservoir containing a Furin/PC inhibitor optionally with carriers, optionally a rate controlling barrier to deliver the Furin/PC inhibitors to the skin of the host at a controlled and predetermined rate over a prolonged period of time, and means to secure the device to the skin.

Formulations that include a Furin/PC inhibitor disclosed herein suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, a Furin/PC inhibitor disclosed herein is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, a pharmaceutical composition described herein is in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of a Furin/PC inhibitor disclosed herein in water soluble form. Additionally, suspensions of a Furin/PC inhibitor disclosed herein is optionally prepared as appropriate oily injection suspensions.

In some embodiments, the Furin/PC inhibitors is administered topically and formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

The Furin/PC inhibitors is also optionally formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Combinations

In certain instances, it is appropriate to a Furin/PC inhibitor disclosed herein in combination with an additional therapeutic agent. Additional therapeutic agents are selected for their particular usefulness against the condition that is being treated. In general, the additional therapeutic agent does not need to be administered in the same pharmaceutical composition, at the same time or via the same route and the Furin/PC inhibitor disclosed herein. In one embodiment, the initial administration is made according to established protocols, and then, based upon the observed effects, the dosage, modes of administration and times of administration, further modified.

In some embodiments, the additional therapeutic agent is administered concurrently (e.g., simultaneously, essentially simultaneously or within the same treatment protocol) or sequentially, depending upon the nature of the disease, the condition of the patient, and the actual choice of compounds used. In certain embodiments, the determination of the order of administration, and the number of repetitions of administration of each therapeutic agent during a treatment protocol, is based upon evaluation of the disease being treated and the condition of the patient.

The dose of the additional therapeutic agent varies depending on the additional therapeutic agent, the disease or condition being treated and so forth.

In some embodiments, the additional therapeutic agent is a chemotherapeutic agent, a steroid, an immunotherapeutic agent, a targeted therapy, or a combination thereof. In some embodiments, the additional therapeutic agent is a B cell receptor pathway inhibitor. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, or a combination thereof. In some embodiments, the additional therapeutic agent is an antibody, B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof.

Additional therapeutic agents that maybe administered in conjunction with a Furin/PC inhibitor disclosed herein include, but are not limited to, Nitrogen Mustards such as for example, bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides such as for example, etoglucid; Other Alkylating Agents such as for example dacarbazine, mitobronitol, pipobroman, temozolomide; Folic Acid Analogues such as for example methotrexate, permetrexed, pralatrexate, raltitrexed; Purine Analogs such as for example cladribine, clofarabine, fludarabine, mercaptopurine, nelarabine, tioguanine; Pyrimidine Analogs such as for example azacitidine, capecitabine, carmofur, cytarabine, decitabine, fluorouracil, gemcitabine, tegafur; Vinca Alkaloids such as for example vinblastine, vincristine, vindesine, vinflunine, vinorelbine; Podophyllotoxin Derivatives such as for example etoposide, teniposide; Colchicine derivatives such as for example demecolcine; Taxanes such as for example docetaxel, paclitaxel, paclitaxel poliglumex; Other Plant Alkaloids and Natural Products such as for example trabectedin; Actinomycines such as for example dactinomycin; Antracyclines such as for example aclarubicin, daunorubicin, doxorubicin, epirubicin, idarubicin, mitoxantrone, pirarubicin, valrubicin, zorubincin; Other Cytotoxic Antibiotics such as for example bleomycin, ixabepilone, mitomycin, plicamycin; Platinum Compounds such as for example carboplatin, cisplatin, oxaliplatin, satraplatin; Methylhydrazines such as for example procarbazine; Sensitizers such as for example aminolevulinic acid, efaproxiral, methyl aminolevulinate, porfimer sodium, temoporfin; Protein Kinase Inhibitors such as for example dasatinib, erlotinib, everolimus, gefitinib, imatinib, lapatinib, nilotinib, pazonanib, sorafenib, sunitinib, temsirolimus; Other Antineoplastic Agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens such as for example diethylstilbenol, ethinylestradiol, fosfestrol, polyestradiol phosphate; Progestogens such as for example gestonorone, medroxyprogesterone, megestrol; Gonadotropin Releasing Hormone Analogs such as for example buserelin, goserelin, leuprorelin, triptorelin; Anti-Estrogens such as for example fulvestrant, tamoxifen, toremifene; Anti-Androgens such as for example bicalutamide, flutamide, nilutamide, Enzyme Inhibitors, aminoglutethimide, anastrozole, exemestane, formestane, letrozole, vorozole; Other Hormone Antagonists such as for example abarelix, degarelix; Immunostimulants such as for example histamine dihydrochloride, mifamurtide, pidotimod, plerixafor, roquinimex, thymopentin; Immunosuppressants such as for example everolimus, gusperimus, leflunomide, mycophenolic acid, sirolimus; Calcineurin Inhibitors such as for example ciclosporin, tacrolimus; Other Immunosuppressants such as for example azathioprine, lenalidomide, methotrexate, thalidomide; and Radiopharmaceuticals such as for example, iobenguane.

Further therapeutic agents that maybe administered in conjunction with a Furin/PC inhibitor disclosed herein include, but are not limited to interferons, interleukins, Tumor Necrosis Factors, Growth Factors, or the like.

Additional therapeutic agents that maybe administered in conjunction with a Furin/PC inhibitor disclosed herein include, but are not limited to, Immunostimulants such as for example ancestim, filgrastim, lenograstim, molgramostim, pegfilgrastim, sargramostim; Interferons such as for example interferon alfa natural, interferon alfa-2a, interferon alfa-2b, interferon alfacon-1, interferon alfa-n1, interferon beta natural, interferon beta-1a, interferon beta-1b, interferon gamma, peginterferon alfa-2a, peginterferon alfa-2b; Interleukins such as for example aldesleukin, oprelvekin; Other Immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; Calcineurin Inhibitors such as for example ciclosporin, tacrolimus; Other Immunosuppressants such as for example azathioprine, lenalidomide, methotrexate, thalidomide.

Further therapeutic agents that maybe administered in conjunction with a Furin/PC inhibitor disclosed herein include, but are not limited to, Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

Additional therapeutic agents that maybe administered in conjunction with a Furin/PC inhibitor disclosed herein include, but are not limited to, Monoclonal Antibodies such as for example alemtuzumab, bevacizumab, catumaxomab, cetuximab, edrecolomab, gemtuzumab, ofatumumab, panitumumab, rituximab, trastuzumab, Immunosuppressants, eculizumab, efalizumab, muromab-CD3, natalizumab; TNF alpha Inhibitors such as for example adalimumab, afelimomab, certolizumab pegol, golimumab, infliximab, Interleukin Inhibitors, basiliximab, canakinumab, daclizumab, mepolizumab, tocilizumab, ustekinuma, Radiopharmaceuticals, ibritumomab tiuxetan, tositumomab; Others Monoclonal Antibodies such as for example abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, zalutumumab.

Further therapeutic agents that maybe administered in conjunction with a Furin/PC inhibitor disclosed herein include, but are not limited to, agents that affect the tumor microenvironment such as cellular signaling network (e.g. phosphatidylinositol 3-kinase (PI3K) signaling pathway, signaling from the B-cell receptor and the IgE receptor). In some embodiments, the second agent is a PI3K signaling inhibitor or a syc kinase inhibitor. In one embodiment, the syk inhibitor is R788. In another embodiment is a PKCγ inhibitor such as by way of example only, enzastaurin.

Examples of agents that affect the tumor micro-environment include PI3K signaling inhibitor, syc kinase inhibitor, Protein Kinase Inhibitors such as for example dasatinib, erlotinib, everolimus, gefitinib, imatinib, lapatinib, nilotinib, pazonanib, sorafenib, sunitinib, temsirolimus; Other Angiogenesis Inhibitors such as for example GT-111, JI-101, R1530; Other Kinase Inhibitors such as for example AC220, AC480, ACE-041, AMG 900, AP24534, Arry-614, AT7519, AT9283, AV-951, axitinib, AZD1152, AZD7762, AZD8055, AZD8931, bafetinib, BAY 73-4506, BGJ398, BGT226, BI 811283, BI6727, BIBF 1120, BIBW 2992, BMS-690154, BMS-777607, BMS-863233, BSK-461364, CAL-101, CEP-11981, CYC116, DCC-2036, dinaciclib, dovitinib lactate, E7050, EMD 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, Btk inhibitor, PF-00562271, PF-02341066, PF-03814735, PF-04217903, PF-04554878, PF-04691502, PF-3758309, PHA-739358, PLC3397, progenipoietin, R547, R763, ramucirumab, regorafenib, RO5185426, SAR103168, SCH 727965, SGI-1176, SGX523, SNS-314, TAK-593, TAK-901, TKI258, TLN-232, TTP607, XL147, XL228, XL281RO5126766, XL418, XL765.

Further examples of therapeutic agents for use in combination with a Furin/PC inhibitor disclosed herein include, but are not limited to, inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other agents that may be employed in combination with a Furin/PC inhibitor disclosed herein include, but are not limited to, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Further therapeutic agents that may be administered in conjunction with a Furin/PC inhibitor disclosed herein include, but are not limited to, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; aza osine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-such as for example growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Other therapeutic agents that maybe administered in conjunction a Furin/PC inhibitor disclosed herein include, but are not limited to, alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of alkylating agents that include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Additional therapeutic agents that maybe administered in conjunction with a Furin/PC inhibitor disclosed herein include, but are not limited to: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Annad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the individual is suffering from or at risk of suffering from an autoimmune disease, or an inflammatory disease a Furin/PC inhibitor disclosed herein may be used in combination with: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

Dosing and Treatment Regimens

Disclosed herein, in certain embodiments, are methods of treating an infectious disease in a mammal in need of such treatment. In some embodiments, the methods comprise administering to the mammal a therapeutically effective amount of a Furin/PC inhibitor disclosed herein. In some embodiments, the infection disease is associated with influenza virus, human immunodeficiency virus 1, Ebola, measles, cytomegalovirus, and flaviviruses (Dengue, Yellow fever, West Nile, Japanese encephalitis and multiple additional related flaviviruses) and parasitic nematodes. In some embodiments, a Furin/PC inhibitor disclosed herein neutralizes an exotoxin selected from the group consisting of anthrax toxin, pseudomonas exotoxin A, Shiga toxin, diphtheria toxin, tetanus and botulism neurotoxins, and combinations thereof. In some embodiments, a Furin/PC inhibitor disclosed herein neutralizes virulence of bacteria carrying the exotoxin.

Further disclosed herein, in certain embodiments, are methods of treating a cancer in a mammal in need thereof. In some embodiments, the methods comprise administering a therapeutically effective amount of a Furin/PC inhibitor disclosed herein. In some embodiments, the cancer is skin tumors, head and neck squamous cell carcinomas, astrocytoma, lung non-small cell carcinoma, or metastasis of colorectal cancer.

Also disclosed herein, in certain embodiments, are methods of treating an autoimmune or inflammatory disease, disorder or condition in a mammal in need thereof. In some embodiments, the methods comprise administering to the mammal a therapeutically effective amount of a Furin/PC inhibitor disclosed herein. In some embodiments, the neurodegenerative disease is arthritis, atherosclerosis, and Alzheimer's disease.

The administration of a Furin/PC inhibitor disclosed herein is optionally administered chronically, that is, for an extended period of time, including throughout the duration of the patient's life in order to ameliorate or otherwise control or limit the symptoms of the patient's disease or condition.

In some embodiments, a Furin/PC inhibitor disclosed herein is given continuously. In some embodiments, administration of a Furin/PC inhibitor disclosed herein is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

In some embodiments, once improvement of a patient's conditions has occurred, maintenance doses of a Furin/PC inhibitor disclosed herein are administered. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

In some embodiments, a pharmaceutical composition described herein is in unit dosage forms suitable for single administration of precise dosages. In unit dosage form, the formulation is divided into unit doses containing appropriate quantities of one or more Furin/PC inhibitors. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

In prophylactic applications, a Furin/PC inhibitor disclosed herein or a pharmaceutical composition containing a Furin/PC inhibitor disclosed herein is administered to an individual susceptible to or otherwise at risk of a particular disease, disorder or condition. In certain embodiments of this use, the precise amounts of a Furin/PC inhibitor disclosed herein depend on an individual's state of health, weight, and the like. Furthermore, in some instances, when a Furin/PC inhibitor disclosed herein or a pharmaceutical composition comprising a Furin/PC inhibitor described herein is administered to an individual, effective amounts for this use depend on the severity and course of the disease, disorder or condition, previous therapy, an individual's health status and response to the drugs, and the judgment of the treating physician.

In certain instances, wherein following administration of a selected dose of a Furin/PC inhibitor disclosed herein or a pharmaceutical composition comprising a Furin/PC inhibitor described herein, an individual's condition does not improve, upon the doctor's discretion the administration of the Furin/PC inhibitor disclosed herein or pharmaceutical composition is optionally administered chronically, that is, for an extended period of time, including throughout the duration of an individual's life in order to ameliorate or otherwise control or limit the symptoms of an individual's disorder, disease or condition.

In certain embodiments, an effective amount of a given agent varies depending upon one or more of a number of factors such as the particular Furin/PC inhibitor disclosed herein, disease or condition and its severity, the identity (e.g., weight) of an individual or host in need of treatment, and is determined according to the particular circumstances surrounding the case, including, e.g., the specific agent being administered, the route of administration, the condition being treated, and an individual or host being treated. In some embodiments, doses administered include those up to the maximum tolerable dose. In certain embodiments, about 0.02 to about 5000 mg per day, from about 1 to about 1500 mg per day, about 1 to about 100 mg/day, about 1 to about 50 mg/day, or about 1 to about 30 mg/day, or about 5 to about 25 mg/day of a Furin/PC inhibitor disclosed herein is administered. In various embodiments, the desired dose is conveniently be presented in a single dose or in divided doses administered simultaneously (or over a short period of time) or at appropriate intervals, for example as two, three, four or more sub-doses per day.

In certain instances, there are a large number of variables in regard to an individual treatment regime, and considerable excursions from these recommended values are considered within the scope described herein. Dosages described herein are optionally altered depending on a number of variables such as, by way of non-limiting example, the activity of a Furin/PC inhibitor disclosed herein, the disease or condition to be treated, the mode of administration, the requirements of an individual, the severity of the disease or condition being treated, and the judgment of the practitioner.

Toxicity and therapeutic efficacy of such therapeutic regimens are optionally determined by pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. In some embodiments, a Furin/PC inhibitor disclosed herein exhibiting high therapeutic indices is preferred. In certain embodiments, data obtained from cell culture assays and animal studies are used in formulating a range of dosage for use in human. In some embodiments, the dosage of a Furin/PC inhibitor disclosed herein lies within a range of circulating concentrations that include the $ED_{50}$ with minimal toxicity. The dosage optionally varies within this range depending upon the dosage form employed and the route of administration utilized.

While some embodiments of the present disclosure have been shown and described herein, such embodiments are provided by way of example only. It is intended that the following claims define the scope of the present disclosure and that methods and structures within the scope of these claims and their equivalents be covered thereby.

What is claimed is:

1. A compound of formula II, or a pharmaceutically acceptable salt, stereoisomer, tautomer, or prodrug thereof:

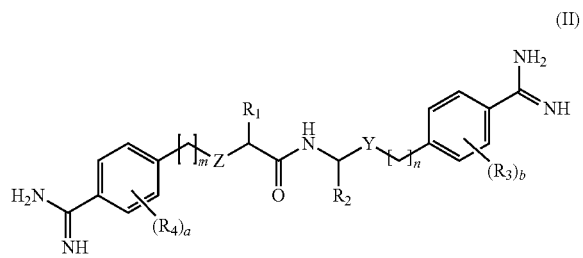

wherein:
$R_1$ is alkyl, cycloalkyl, or heteroalicyclyl;
$R_2$ is —U-guanidine, wherein U is alkyl, cycloalkyl, heteroalicyclyl, aryl, or heteroaryl;
Y is —CONH—, —SO$_2$NH—, —O—, —CH$_2$—, —s—, —SO$_2$—, or —COSO$_2$NH—;
Z is —CONH—, —SO$_2$NH—, —o—, —CH$_2$—, —s—, —SO$_2$—, or —COSO$_2$NH—;
$R_3$ and $R_4$ are each independently —F, —CF$_3$, —OCF$_3$, —OCH$_3$, or alkyl;
a and b are each independently 0, 1, or 2; and
m and n are each independently 0, 1, 2, or 3.

2. The compound of claim 1, or a pharmaceutically acceptable salt, stereoisomer, tautomer, or prodrug thereof, wherein $R_1$ is $C_1$-$C_6$ alkyl.

3. The compound of claim 1, or a pharmaceutically acceptable salt, stereoisomer, tautomer, or prodrug thereof, wherein $R_1$ is isopropyl.

4. The compound of claim 1, or a pharmaceutically acceptable salt, stereoisomer, tautomer, or prodrug thereof, wherein U is $C_1$-$C_6$ alkyl.

5. The compound of claim 4, or a pharmaceutically acceptable salt, stereoisomer, tautomer, or prodrug thereof, wherein U is —(CH$_2$)$_3$—.

6. The compound of claim 1, or a pharmaceutically acceptable salt, stereoisomer, tautomer, or prodrug thereof, wherein Y is —CONH—.

7. The compound of claim 1, or a pharmaceutically acceptable salt, stereoisomer, tautomer, or prodrug thereof, wherein Z is —SO$_2$NH—.

8. The compound of claim 1, or a pharmaceutically acceptable salt, stereoisomer, tautomer, or prodrug thereof, wherein m is 1 and n is 1.

9. The compound of claim 1, or a pharmaceutically acceptable salt, stereoisomer, tautomer, or prodrug thereof, wherein a and b are 0.

10. The compound of claim 1, or a pharmaceutically acceptable salt, stereoisomer, tautomer, or prodrug thereof, wherein the compound is
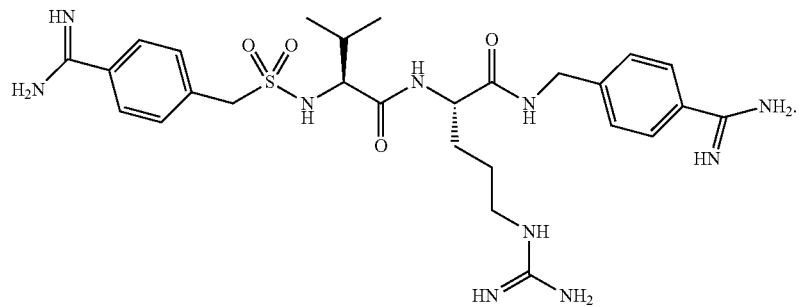 [SMILES: CC(C)[C@H](NS(=O)(=O)Cc1ccc(C(=N)N)cc1)C(=O)N[C@@H](CCCNC(=N)N)C(=O)NCc1ccc(C(=N)N)cc1]
11. A pharmaceutical composition comprising a compound of claim 1, or a pharmaceutically acceptable salt, stereoisomer, tautomer, or prodrug thereof, and a pharmaceutically acceptable carrier thereof.
* * * * *